US012215186B2

(12) United States Patent
Sharpe et al.

(10) Patent No.: US 12,215,186 B2
(45) Date of Patent: Feb. 4, 2025

(54) PROCESS FOR MAKING NOVEL POLYCONDENSATION PRE-POLYESTERS, OTHER COPOLYESTER PRECURSORS, AND COPOLYESTERS

(71) Applicant: Eastman Chemical Company, Kingsport, TN (US)

(72) Inventors: Robert Jacks Sharpe, Madison, AL (US); Emmett Dudley Crawford, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 521 days.

(21) Appl. No.: 17/596,690

(22) PCT Filed: Jun. 26, 2020

(86) PCT No.: PCT/US2020/039742
§ 371 (c)(1),
(2) Date: Dec. 16, 2021

(87) PCT Pub. No.: WO2020/264244
PCT Pub. Date: Dec. 30, 2020

(65) Prior Publication Data
US 2022/0363816 A1    Nov. 17, 2022

Related U.S. Application Data

(60) Provisional application No. 62/868,314, filed on Jun. 28, 2019, provisional application No. 62/868,299, filed on Jun. 28, 2019.

(51) Int. Cl.
| | | |
|---|---|---|
| *C08G 63/183* | (2006.01) | |
| *C07C 69/75* | (2006.01) | |
| *C07C 69/82* | (2006.01) | |
| *C07D 307/68* | (2006.01) | |
| *C08G 63/199* | (2006.01) | |

(52) U.S. Cl.
CPC .......... *C08G 63/183* (2013.01); *C07C 69/75* (2013.01); *C07C 69/82* (2013.01); *C07D 307/68* (2013.01); *C08G 63/199* (2013.01); *C07C 2601/04* (2017.05); *C07C 2601/14* (2017.05); *C07C 2601/16* (2017.05)

(58) Field of Classification Search
CPC .......... C07C 2601/04; C07C 2601/14; C07C 2601/16; C07C 69/75; C07C 69/80; C07C 69/82; C07D 307/68; C08G 63/16; C08G 63/183; C08G 63/199
See application file for complete search history.

(56) References Cited

U.S. PATENT DOCUMENTS

| | | |
|---|---|---|
| 2,012,267 A | 8/1935 | Carothers |
| 4,096,341 A | 6/1978 | Frazer |
| 4,617,369 A | 10/1986 | Huynh-Ba |
| 4,997,910 A | 3/1991 | Garapon et al. |
| 5,104,842 A | 4/1992 | Garapon et al. |
| 6,469,133 B2 | 10/2002 | Baker et al. |
| 2022/0363816 A1* | 11/2022 | Sharpe ............... C08G 63/199 |
| 2023/0002308 A1* | 1/2023 | Sharpe ............... C08G 63/183 |

FOREIGN PATENT DOCUMENTS

| | | | |
|---|---|---|---|
| DE | 23 48 252 A1 | | 4/1974 |
| GB | 1 390 793 A | | 4/1975 |
| JP | H06 100672 A | | 4/1994 |
| JP | H06100672 | * | 4/1994 |
| WO | WO 2017 029479 A1 | | 2/2017 |
| WO | WO 2019 046061 A1 | | 3/2019 |

OTHER PUBLICATIONS

Graffner-Nordberg, M., et al.; "Computational Predictions of Binding Affinities to Dihydrofolate Reductase: Synthesis and Biological Evaluation of Methotrexate Analogues"; Journal of Medicinal Chemistry; 2000, 43, pp. 3852-3861.
Notification of Transmittal of the International Search Report and the Written Opinion of the International Searching Authority, or the Declaration date of mailing Sep. 2, 2020 received in International Application No. PCT/US2020/039740.
Notification of Transmittal of the International Search Report and the Written Opinion of the International Searching Authority, or the Declaration date of mailing Sep. 8, 2020 received in International Application No. PCT/US2020/039742.
U.S. Appl. No. 17/596,696, filed Dec. 16, 2021; Sharpe and Crawford; now U. S. Publication No. 2023-0002308.

* cited by examiner

*Primary Examiner* — Frances Tischler
*Assistant Examiner* — Gennadiy Mesh
(74) *Attorney, Agent, or Firm* — Tammye L. Taylor Polk

(57) ABSTRACT

A process for making a polycondensation pre-polyester, a polyester or both, comprising the following steps: following steps: A. Acylation of at least one diacid chloride with at least one alcohol to form at least one diester; B. Partial hydrolysis of the diester product of Step A to form at least one monoacid; C. Esterifying the monoacid of Step B with at least one diol to form a diester; D. Reacting the diester of Step C under acidic conditions to form a diacid; and subsequently, performing either Step E or Step F as follows: E. Bisalkylation of the diacid of Step D with at least one haloalcohol to form a pentamer, or F. Esterifiying the diacid of Step D under esterification conditions with at least one diol to form a pentamer, provided that the diol is not the same as the diol used in Step C.

20 Claims, No Drawings

PROCESS FOR MAKING NOVEL POLYCONDENSATION PRE-POLYESTERS, OTHER COPOLYESTER PRECURSORS, AND COPOLYESTERS

CROSS-REFERENCE TO RELATED APPLICATIONS

This application is a national stage filing under 35 USC § 371 of International Application Number PCT/US2020/039742, filed on, Jun. 26, 2020 which claims the benefit of the filing date to U.S. Provisional Application Nos. 62/868,314 and 62/868,299, both filed on Jun. 28, 2019, the entire disclosures of which are incorporated by reference herein.

FIELD OF THE INVENTION

The invention provides processes for making novel polycondensation prepolyesters, other copolyester precursors, and/or copolyesters made therefrom. It is believed that these copolyester precursors can provide access to perfectly alternating copolyesters with respect to diol residues upon polymerization/polycondensation.

BACKGROUND OF THE INVENTION

Polyesters that are homopolymers have perfectly alternating repeat units with respect to diol residues. Indeed, that is the only configuration that homopolymers are known to have.

In U.S. Pat. No. 4,997,910, a process is disclosed for condensing at least one epoxide and at least one cyclic anhydride of a dicarboxylic acid in the presence of a catalyst consisting of at least one certain titanium peroxidic complex wherein the process is said to result in a perfectly alternate polyester.

The process of polycondensation of copolyesters is typically known to produce a randomly selected order of repeat units of diol residues in the final copolyester.

There is a commercial need for processes to make copoolyester precursors and copolyesters (which undergo polycondensation) where the copolyesters have properties such as the following (1) ability for targeted synthesis, (2) requires less diol residues to make the copolyesters, and (3) perfectly alternating repeat units of diol residues.

SUMMARY OF THE INVENTION

In view of the above commercial shortcomings in the art, the present disclosure addresses the need for processes of making copolyesters and copolyester precursors where the copolyesters have one or more of the following properties: (1) ability for targeted synthesis, (2) requires less diol residues to make the copolyesters, and/or (3) perfectly alternating repeat units of diol residues. It is contemplated that a large number of these types of molecules may be prepared via this synthetic method.

For the ease of reference but not intending to be limiting in any way, certain aspects of this disclosure are numbered consecutively, as follows:

In aspect 1, this invention relates to a process for making a polycondensation pre-copolyester, a copolyester, and/or other copolyester precursors, comprising the following steps:
  A. Acylation of at least one diacid chloride with at least one alcohol to form at least one diester;
  B. Partial hydrolysis of the diester product of Step A to form at least one monoacid;
  C. Esterifying the monoacid of Step B with at least one diol to form a diester;
  D. Reacting the diester of Step C under acidic conditions to form a diacid; and subsequently, performing either Step E or Step F as follows:
  E. Bisalkylation of the diacid of Step D with at least one haloalcohol to form a pentamer, or
  F. Esterifiying the diacid of Step D under esterification conditions with at least one diol to form a pentamer, provided that the diol is not the same as the diol used in Step C.

In aspect 2, the invention relates to a process for making a polycondensation pre-polyester, a polyester, and/or other polyester precursors, comprising the following steps:
  A. Acylation of at least one diacid chloride to form at least one diester, comprising the following steps:
    1. Adding at least one alcohol, at least one base, and optionally, at least one aprotic solvent to a first reaction zone;
    2. Adding at least one aprotic solvent and at least one diacid chloride to a second reaction zone;
    3. Feeding the contents in the first reaction zone into the second reaction zone;
  B. Partial hydrolysis of the diester product of Step A to form at least one monoacid comprising the following steps:
    1. adding the product of Step A and at least one aprotic solvent to a third reaction zone;
    2. adding at least one base, water, and at least one alcohol to a fourth reaction zone;
    3. Feeding the contents in the fourth reaction zone into the third reaction zone; and
  C. Esterifying the monoacid of Step B to form a diester comprising the following steps:
    1. Add the monoacid of Step B, at least one diol, at least one catalyst (4-dimethylaminopyridine), at least one aprotic solvent and at least one carbodiimide and react under esterification conditions;
  D. Reacting the diester of Step C under acidic conditions to form a diacid, comprising the following steps:
    1. Reacting the diester of Step C with at least one acid, for example, a Lewis acid such as iodine, and at least one aprotic solvent; and then performing either Step E or Step F as follows:
  E. Bisalkylation of the diacid of Step D to form a pentamer comprising the following step: dissolve the diacid of Step D with at least one aprotic solvent, add at least one base, and then react with at least one haloalcohol; or
  F: Esterifiying the diacid of Step D to form a pentamer comprising the following step: dissolve the diacid of Step D in at least one aprotic solvent and react with at least one diol, and at least one carbodiimide, with at least one catalyst (e.g., 4-dimethylaminopyridine), provided that the diol is not the same as in Step C.

In aspect 3 of the process of the invention, at least one diacid chloride of Step A in either of aspects 1 and 2 of the invention can be selected from the group consisting of terephthaloyl chloride, isophthaloyl chloride, cyclohexane-1,4-dicarbonyl chloride, furan-2,5-dicarbonyl chloride, adipoyl chloride, and sebacoyl chloride. In one aspect, at least one diacid chloride can be used and can be selected from terephthaloyl chloride, cyclohexane-1,4-dicarbonyl chloride, and furan-2,5-dicarbonyl chloride.

In aspect 4 of the invention, the alcohol of Step A(1) of any one of aspects 2 and 3 of the invention can be selected from the group consisting of tert-butanol, methanol, ethanol and benzyl alcohol.

In aspect 5 of the invention, the base of Step A(1) of any one of aspects 2-4 is at least one base which can be selected from pyridine, (such as 4-dimethylaminopyridine), triethylamine, diisopropylethylamine.

In aspect 6 of the invention, the aprotic solvent of Steps A(1) and (2) of any one of aspects 2-5 can be selected from the group consisting of methylene chloride, hexane, benzene, toluene, 1,4-dioxane, chloroform, diethyl ether, dichloromethane, N-methylpyrrolidone, tetrahydrofuran, ethyl acetate, acetone, dimethylformamide, acetonitrile, and dimethyl sulfoxide; in one aspect, the aprotic solvent of Steps A (1) and (2) can be methylene chloride.

In aspect 7 of the invention, subsequent to Step A (3) of any one of aspects 2-6 of the invention, and after the reaction goes below the reflux temperature, the temperature can be adjusted to 30 to 50° C. and can be held for about 5-15 hours under continuous stirring.

In aspect 8 of the invention, the diester product of Step A of any of aspects 1-7 of the invention can be any diester of the invention, for example, 1,4-di-tert-butyl terephthalate diester.

In aspect 9 of the invention, the aprotic solvent of Step B (1) and (2) of any one of aspects 2-8 of the invention can include but is not limited to methylene chloride, toluene, tetrahydrofuran, acetonitrile, dioxane, or acetone; in one aspect, the aprotic solvent of Step B(1) can be toluene.

In aspect 10 of the invention, the base of Step B(2) of any of aspects 2-9 of the invention can be selected from potassium hydroxide or sodium hydroxide; in one aspect, the base of Step B(2) can be potassium hydroxide.

In aspect 11 of the invention, the alcohol of Step B of any one of aspects 1-10 of the invention can be selected from the group consisting of tert-butanol, methanol, ethanol and benzyl alcohol; in one aspect, the alcohol of Step B can be methanol.

In aspect 12 of the invention, at least one monoacid of Steps B and C of any one of aspects 1-11 of the invention can be selected from 4-tert-butoxycarbonyl)benzoic acid, 4-(tert-butoxycarbonyl)cyclohexane-1-carboxylic acid), or 5-(tert-butoxycarbonyl)furan-2-carboxylic acid, tert-methoxycarbonyl)benzoic acid, 4-(tert-methoxycarbonyl) cyclohexane-1-carboxylic acid), or 5-(tert-methoxycarbonyl)furan-2-carboxylic acid, tert-ethoxycarbonyl)benzoic acid, 4-(tert-ethoxycarbonyl)cyclohexane-1-carboxylic acid), or 5-(tert-ethoxycarbonyl)furan-2-carboxylic acid, tert-benzyloxycarbonyl)benzoic acid, 4-(tert-benzyloxycarbonyl)cyclohexane-1-carboxylic acid), or 5-(tert-benzyloxycarbonyl)furan-2-carboxylic acid; in one aspect, the at least one monoacid of Steps B and C is 4-tert-butoxycarbonyl) benzoic acid.

In aspect 13 of the invention, at least one diol of Step C of any one of aspects 1-12 of the invention can be selected from residues of at least one diol as follows: 2,2,4,4-tetramethylcyclobutane-1,3-diol, 2,2-dimethyl-1,3-propanediol, 1,2-cyclohexanedimethanol, 1,3-cyclohexanedimethanol, 1,4-cyclohexanedimethanol, 2,2,4-trimethyl-1,3-pentanediol, hydroxypivalyl hydroxypivalate, 2-methyl-1,3-propanediol, 2-butyl-2-ethyl-1,3-propanediol, 1,4-butanediol, 1,3-propanediol, 1,5-pentanediol, 1,6-hexanediol, ethylene glycol, diethylene glycol, triethylene glycol, isosorbide, 1,6-hexanediol, 3-methyl-pentanediol, 2-methylpentanediol, 2,2,4-tri-methylpentane-diol, 2-ethylhexanediol, 2,2-diethylpropanediol, 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, resorcinol, 4,4'-(propane-2,2-diyl)dicyclohexanol, or 2,2-bis-(4-hydroxypropoxyphenyl)-propane.

In aspect 14 of the invention, at least one diol of Step C of aspect 13 of the invention can be selected from at least one of 2,2,4,4-tetramethylcyclobutane-1,3-diol, 2,2-dimethyl-1,3-propanediol, 1,4-cyclohexanedimethanol, ethylene glycol, propylene glycol, 1,3-propanediol, butanediol, resorcinol or 4,4'-(propane-2,2-diyl)dicyclohexanol.

In aspect 15 of the invention, at least one diol of Step C of aspect 14 of the invention can be 2,2,4,4-tetramethylcyclobutane-1,3-diol.

In aspect 16 of the invention, at least one diol of Step C of aspect 14 of this invention can be 1,4-cyclohexanedimethanol.

In aspect 17 of the invention, at least one diol of Step C of any one of aspects 1-16 can be selected from at least one of 2,2,4,4-tetramethylcyclobutane-1,3-diol and 1,4-cyclohexanedimethanol; in one aspect, diols of Step C can be selected from at least one of 2,2,4,4-tetramethylcyclobutane-1,3-diol and ethylene glycol; in one aspect, the diols of Step C can be selected from at least one of 2,2,4,4-tetramethylcyclobutane-1,3-diol, 1,4-cycohexanedimethanol and ethylene glycol; in one aspect, the diols of Step C can be selected from at least one of 1,4-cycloehexanedimethanol and ethylene glycol; in one aspect, the diols of Step C can be selected from at least one of ethylene glycol, propylene glycol, 1,3-propanediol, or butanediol; in one aspect, at least one diol of Step C can be ethylene glycol; in one aspect, at least one diol of Step C can be isosorbide.

In aspect 18 of the invention, at least one carbodiimide of Step C of any one of aspects 1-17 of the invention can be selected from diisopropylcarbodiimide and dicyclohexylcarbodiimide; in one aspect, the carbodiimide of Step C can be diisopropylcarbodiimide.

In aspect 19 of the invention, the aprotic solvent of Step C of any one of aspects 1-18 of the invention can be selected from methylene chloride or dimethylformamide; in one aspect, the aprotic solvent of Step C is methylene chloride.

In aspect 20 of the invention, the aprotic solvent of Step D of any one of aspects 1-19 of the invention can be acetonitrile.

In aspect 21 of the invention, the diacid product of Step D of any one of aspects 1-20 of the invention can be selected from 4,4'-(2,2,4,4-tetramethylcyclobutane-1,3-diyl)bis(oxy) bis(carbonyl)dibenzoic acid, 4,4'-(cyclohexane-1,4-diyl)bis (methylene)bis(oxy)bis(carbonyl)dibenzoic acid; 4,4'-(propane-2,2-diylbis(cyclohexane-4,1-diyl)bis(oxy)bis (carbonyl)dibenzoic acid); and 4,4'-(1,3-phenylenebis(oxy) bis(carbonyl)dibenzoic acid; in one aspect, the diacid product of Step D can be 4,4'-(2,2,4,4-tetramethylcyclobutane-1,3-diyl)bis(oxy)bis(carbonyl)dibenzoic acid.

In aspect 22 of the invention, the polycondensation prepolyester of Step D of any of aspects 1-21 of the invention can be selected from [bis(2-hydroxyethyl) O,O'-(2,2,4,4-tetramethylcyclobutane-1,3-diyl)diterephthalate; 4,4'-bis(2-hydroxyethyl) O'1,O1-(2,2,4,4-tetramethylcyclobutane-1,3-diyl)bis(cyclohexane-1,4-dicarboxylate); 5,5'-bis(2-hydroxyethyl) O'2,O2-(2,2,4,4-tetramethylcyclobutane-1,3-diyl)bis(furan-2,5-dicarboxylate); O,O'-(cyclohexane-1,4-diylbis(methylene)bis(2-hydroxyethyl)diterephthalate); and bis(2-hydroxyethyl) O,O'-(propane-2,2-diyl-bis(cyclohexane-4,1-diyl)diterephthalate).

In aspect 23 of the invention, the process of any one aspects 1-22 of the invention can also comprises Step E:

dissolving the diacid of Step D of the process of the invention with at least one aprotic solvent, e.g., 4-dimethylaminopyridine, and reacting with at least one haloalcohol and at least one carbodiimide, for example, diisopropylcarbodiimide and dicyclohexylcarbodiimide; in one aspect, the aprotic solvent of Step E can be dimethylformamide.

In aspect 24 of the invention, at least one base of Step E of any one of aspects 1-23 of the invention can be selected from potassium carbonate, sodium carbonate, or cesium carbonate; or in one aspect, at least one base of Step E can be potassiym carbonate.

In aspect 25 of the invention, at least one haloalcohol of Step E of any one of aspects 1-24 of the invention can be selected from a bromoalcohol or a chloroalcohol.

In aspect 26 of the invention, at least one haloalcohol of Step E of aspect 25 can be selected from 2-bromoethanol, 3-bromopropanol, 4-bromobutanol, 5-bromopentanol, 6-bromohexanol, 2-chloroethanol, 3-chloropropanol, 4-chlorobutanol, 5-chloropentanol, or 6-chlorohexanol; in one aspect, at least one haloalcohol can be 2-bromoethanol.

In aspect 27 of the invention, at least one aprotic solvent of Step F of any one of aspects 1-26 of the invention can be dimethylformamide.

In one aspect 28 of the invention, at least one carbodiimide of Step F of any one of aspects 1-27 can be selected from diisopropylcarbodiimide and dicyclohexylcarbodiimide.

In aspect 29 of the invention, the carbodiimide of Step F of any one of aspects 1-28 of the invention can be diisopropylcarbodiimide.

In aspect 30 of the invention, the diol of Step F of any one of aspects 1-29 of the invention can be the same as those of Step C of the process of the invention.

In aspect 31 of the invention, the reaction mixture can be allowed to stir at room temperature for 5 to 20 (12) hours.

In aspect 32 of the invention, this invention provides at least one trimer or at least one pentamer formed using any of the processes of the invention. These trimers and pentamers can include but is not limited to any of those described herein. In aspect 32, where the invention provides at least one copolyester comprising the trimer and pentamer of the invention, the copolyester of this aspect 32 may not be perfectly alternating with respect to diol residues as defined herein; however, the R substituent cannot be located next to or adjoining another R substituent in the polymer chain while the R" substituent can be located next to or adjoining another R" substituent in the polymer chain.

In aspect 33 of the invention, at least one pentamer made from any of the processes of the invention can include but are not limited to [bis(2-hydroxyethyl) O,O'-(2,2,4,4-tetramethylcyclobutane-1,3-diyl)diterephthalate; 4,4'-bis(2-hydroxyethyl) O'1,O1-(2,2,4,4-tetramethylcyclobutane-1,3-diyl) bis(cyclohexane-1,4-dicarboxylate); 5,5'-bis(2-hydroxyethyl) O'2,O2-(2,2,4,4-tetramethylcyclobutane-1,3-diyl)bis(furan-2,5-dicarboxylate); O,O'-(cyclohexane-1,4-diylbis(methylene)bis(2-hydroxyethyl)diterephthalate); bis(2-hydroxyethyl) O,O'-(propane-2,2-diyl-bis(cyclohexane-4,1-diyl)diterephthalate), and O,O'-(1,3-phenylene)bis(2-hydroxyethyl)diterephthalate), in one aspect, the pentamer can be O,O'-(1,3-phenylene)bis(2-hydroxyethyl)diterephthalate).

In aspect 34 of the invention, at least one copolyester can be prepared according to any of the processes of the invention. This copolyester can comprise perfectly alternating repeat units. This copolyester can be made from at least one pentamer of the invention and comprise perfectly alternating repeat units.

In one aspect, any one of the pentamers made using the process of the invention can contain substantially no active catalyst or no active catalyst. By "no active catalyst", it is meant that the pentamer itself is unreactive when exposed to conditions standard in the art for polymerization.

Novel diester intermediates, monoacids, and diacids can be formed using the processes of the invention. These novel diester intermediates, monoacids, and/or diacids can be used to make the copolyesters of the invention.

In one aspect, the processes of the invention can employ the use of catalysts including but not limited to at least one of germanium, antimony and gallium, or combinations thereof or derivatives thereof.

In one aspect, the copolyester compositions of the invention can include germanium, antimony and gallium or combinations thereof or derivatives thereof.

In one aspect, there can be less than 10 mole % loss, or less than 9 mole % loss, or less than 8 mole % loss, or less than 7 mole % loss, or less than 6 mole %, or less than 5 mole % loss of the diol residues of Step C during polymerization.

In one aspect, this invention provides at least one diacid of used to make the diester intermediates of the invention.

In one aspect, this invention provides at least one diester intermediate of used to make any of the pentamer of the invention.

In one aspect, this invention provides any of the pentamers of the invention used to make any copolyesters of the invention using polycondensation.

In one aspect, this invention provides at least one copolyester prepared from any one of the diacid intermediates of the invention, trimers of the invention, diester intermediates of the invention or pentamers of the invention.

In one aspect, this invention provides copolyesters which can comprise perfectly alternating repeat units prepared by the processes of the invention, or alternatively, can comprise copolyesters which may not be perfectly alternating as described in aspect 32 herein.

DETAILED DESCRIPTION

The present invention may be understood more readily by reference to the following detailed description of certain embodiments of the invention and the working examples. In accordance with the purpose(s) of this invention, certain embodiments of the invention are described in the Summary of the Invention and are further described herein below. Also, other embodiments of the invention are described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons," is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the claims, the singular forms "a," "an" and "the" include their plural references unless the context clearly dictates otherwise. References to a composition or process containing or including "an" ingredient or "a" step is intended to include other ingredients or other steps, respectively, in addition to the one named.

The terms "containing" or "including," are synonymous with the term "comprising," and is intended to mean that at least the named compound, element, particle, or method step, etc., is present in the composition or article or method, but does not exclude the presence of other compounds, catalysts, materials, particles, method steps, etc., even if the other such compounds, material, particles, method steps, etc., have the same function as what is named, unless expressly excluded in the claims.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and the recited lettering can be arranged in any sequence, unless otherwise indicated.

The term "copolyester," as used herein is understood to mean a synthetic polymer prepared by the reaction of one or more difunctional carboxylic acids and/or multifunctional carboxylic acids with one or more difunctional hydroxyl compounds and/or multifunctional hydroxyl compounds except that residues of at least two or more diacids or at least two or more diols, or a combination thereof, are present in the copolyester. Typically, the difunctional carboxylic acid can be a dicarboxylic acid and the difunctional hydroxyl compound can be a dihydric alcohol such as, for example, glycols.

Furthermore, as used in this application, the interchangeable terms "diacid" or "dicarboxylic acid" include multifunctional acids, such as branching agents. The term "glycol" as used in this application includes, but is not limited to, diols, glycols, and/or multifunctional hydroxyl compounds. Alternatively, the difunctional carboxylic acid may be a hydroxy carboxylic acid such as, for example, p-hydroxybenzoic acid, and the difunctional hydroxyl compound may be an aromatic nucleus bearing 2 hydroxyl substituents such as, for example, hydroquinone. The term "residue," as used herein, means any organic structure incorporated into a polymer through a polycondensation and/or an esterification reaction from the corresponding monomer. The term "repeating unit," as used herein, means an organic structure having a dicarboxylic acid residue and a diol residue bonded through an ester group. Thus, for example, the dicarboxylic acid residues may be derived from a dicarboxylic acid monomer or its associated acid halides, esters, half-esters, salts, half-salts, anhydrides, mixed anhydrides, or mixtures thereof, useful in a reaction process with a diol to make polyester. As used herein, the term "terephthalic acid" is intended to include terephthalic acid itself and residues thereof as well as any derivative of terephthalic acid, including its associated acid halides, esters, half-esters, salts, half-salts, anhydrides, mixed anhydrides, or mixtures thereof or residues thereof useful in a reaction process with a diol to make polyester. The term "modifying aromatic diacid" means an aromatic dicarboxylic acid other the terephthalic acid. The term "modifying glycol" means a glycol other than 1,4-cyclohexanedimethanol. In one embodiment, terephthalic acid may be used as the starting material. In another embodiment, dimethyl terephthalate may be used as the starting material. In another embodiment, mixtures of terephthalic acid and dimethyl terephthalate may be used as the starting material and/or as an intermediate material. For the purposes of this invention, polyesterethers are included within the definition of polyesters within the scope of this invention.

The copolyesters of the present invention can be readily prepared by methods well known in the art, for example, as described in U.S. Pat. No. 2,012,267, incorporated herein by reference in its entirety. More particularly, the reactions for preparing the copolyesters can be carried out at temperatures of about 150° C. to about 300° C. in the presence of polycondensation catalysts such as titanium tetrachloride, manganese diacetate, antimony oxide, dibutyl tin diacetate, zinc chloride, or combinations thereof. The catalysts are typically employed in amounts of 10 to 1000 ppm, based on total weight of the reactants.

However, this invention provides new processes for making polycondensation copolyesters as well as their precursors.

A long list of pre-polymerization precursors has been prepared which are expected to assist in facilitating the preparation of copolyesters with a high alternating character. Given the ease of preparation of the examples described herein, it is believed that this synthetic approach could be further extended to an even larger variety of pre-polymerization monomer compounds (including monomers of greater chain length and complexity) which are included within the scope of this invention.

In one embodiment, the pentamers of the invention can comprise at least one of the following structures:

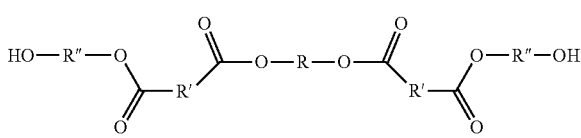

wherein R and R" represent residues of at least one diol;
wherein R and R" are not the same; and
wherein R' comprises residues of at least one diacid or diester.

In one embodiment, the pentamers of the invention can comprise one or more diols selected from residues of 2,2,4,4-tetramethylcyclobutane-1,3-diol, 2,2-dimethyl-1,3-propanediol, 1,2-cyclohexanedimethanol, 1,3-cyclohexanedimethanol, 1,4-cyclohexanedimethanol, 2,2,4-trimethyl-1,3-pentanediol, hydroxypivalyl hydroxypivalate, 2-methyl-1,3-propanediol, 2-butyl-2-ethyl-1,3-propanediol, 1,4-butanediol, 1,3-propanediol, 1,5-pentanediol, 1,6-hexanediol, ethylene glycol, diethylene glycol, triethylene glycol, isosorbide, 1,6-hexanediol, 3-methyl-pentanediol, 2-methylpentanediol, 2,2,4-tri-methylpentane-diol, 2-ethylhexanediol, 2,2-diethylpropanediol, 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, or 2,2-bis-(4-hydroxypropoxyphenyl)-propane. In one embodiment, R or R" can be selected from residues of at least one of 2,2,4,4-tetramethylcyclobutane-1,3-diol, 2,2-dimethyl-1,3-propanediol, 1,4-cyclohexanedimethanol, ethylene glycol, propylene glycol, 1,3-propanediol, butanediol, or combinations thereof. In one embodiment, R or R" can be selected from residues of at least one of 2,2,4,4-tetramethylcyclobutane-1,3-diol and 1,4-cyclohexanedimethanol. In one embodiment, R or R" can be selected from residues of 2,2,4,4-tetramethylcyclobutane-1,3-diol. In one embodiment, R or R" can be selected from residues of 1,4-cyclohexanedimethanol. In one embodiment, R or R" can be selected from residues of at least one of ethylene glycol, propylene glycol, 1,3-propanediol, and butanediol. In one embodiment, R or R" can comprise residues of ethylene glycol.

In one embodiment, at least one pentamer of the invention can comprise R' which further comprises residues of at least one of the following diacids: terephthalic acid, isophthalic acid, cyclohexane-1,4-dicarboxylic acid, furan-2,5-dicarboxylic acid, adipic acid, sebacic acid, or esters derived therefrom or combinations thereof. In one embodiment, R' comprises residues of at least one of the following: terephthalic acid, isophthalic acid, cyclohexane-1,4-dicarboxylic acid, furan-2,5-dicarboxylic acid or any esters derived therefrom. In one embodiment, R' can comprise residues of terephthalic acid or any esters derived therefrom.

Examples of pentamers of the invention can be [bis(2-hydroxyethyl) O,O'-(2,2,4,4-tetramethylcyclobutane-1,3-diyl)diterephthalate; 4,4'-bis(2-hydroxyethyl) O'1,O1-(2,2,4,4-tetramethylcyclobutane-1,3-diyl)bis(cyclohexane-1,4-dicarboxylate); 5,5'-bis(2-hydroxyethyl) O'2,O2-(2,2,4,4-tetramethylcyclobutane-1,3-diyl)bis(furan-2,5-dicarboxylate); O,O'-(cyclohexane-1,4-diylbis(methylene) bis(2-hydroxyethyl)diterephthalate); bis(2-hydroxyethyl) O,O'-(propane-2,2-diyl-bis(cyclohexane-4,1-diyl)diterephthalate), and O,O'-(1,3-phenylene)bis(2-hydroxyethyl)diterephthalate).

Typically, the copolyesters of the invention are prepared through polycondensation.

In one embodiment, the invention provides at least one copolyester comprising repeat units of the following structure:

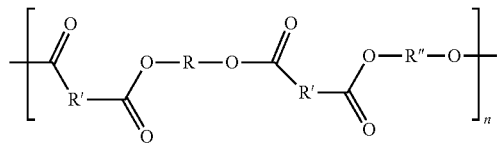

wherein R and R" represent residues of at least one diol; and
wherein R and R" are not the same; and
wherein R' comprises residues of at least one diacid or diester;
and
wherein n represents number of repeat units; in one embodiment, n represents 1-150 or 1-100 or 50-100 repeat units.

In one embodiment of the invention, at least one copolyester is provided that has perfectly alternating repeat units of diol residues or at least 95% of perfectly alternating repeat units of diol residues. Perfectly alternating repeat units of diol residues means that the R substituent appears first in the order of the repeat units for the polymer chain and the R" substituent appears next to and after the R substituent in the polymer chain; in other words, the diol residues will repeat as R, R", R, R", R, R" . . . and so on, in the structure shown in the previous paragraph; therefore the resulting copolyester can be said to be perfectly alternating with respect to the arrangement of the diol residues.

In one embodiment, the copolyester of the invention can be prepared from at least one of the pentamers of the invention.

In one embodiment, the invention provides at least one trimer having the following structure and any pentamer or copolyester made therefrom:

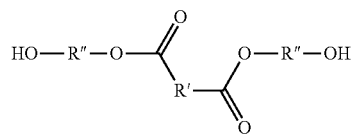

wherein R and R" represent residues of at least one diol provided that R and R" are not the same; and
wherein R' comprises residues of at least one diacid or at least one diester.

In one embodiment, invention provides at least one copolyester comprising the trimer or pentamer of the invention described herein. In one embodiment, this copolyester may not be perfectly alternating with respect to diol residues as defined herein; however, in this case, the R substituent cannot be located next to or adjoining another R substituent in the polymer chain while the R" substituent can be located next to or adjoining another R" substituent in the polymer chain.

In one embodiment, this invention provides at least one copolyester comprising at least one diol selected from residues of 2,2,4,4-tetramethylcyclobutane-1,3-diol, 2,2-dimethyl-1,3-propanediol, 1,2-cyclohexanedimethanol, 1,3-cyclohexanedimethanol, 1,4-cyclohexanedimethanol, 2,2,4-trimethyl-1,3-pentanediol, hydroxypivalyl hydroxypivalate, 2-methyl-1,3-propanediol, 2-butyl-2-ethyl-1,3-propanediol, 1,4-butanediol, 1,3-propanediol, 1,5-pentanediol, 1,2-propanediol, 1,6-hexanediol, ethylene glycol, diethylene glycol, triethylene glycol, isosorbide, 1,6-hexanediol, 3-methylpentanediol, 2-methylpentanediol, 2,2,4-tri-methylpentanediol, 2-ethylhexanediol, 2,2-diethylpropanediol, 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, or 2,2-bis-(4-hydroxypropoxyphenyl)-propane.

In one embodiment, R of the copolyester is selected from residues of at least one of 2,2,4,4-tetramethylcyclobutane-1,3-diol, 2,2-dimethyl-1,3-propanediol, and 1,4-cyclohexanedimethanol or combinations thereof; alternatively, R can be selected from residues of at least one of 2,2,4,4-tetramethylcyclobutane-1,3-diol and 1,4-cyclohexanedimethanol; alternatively, R can selected from residues of 2,2,4,4-tetramethylcyclobutane-1,3-diol; and alternatively, R can be selected from residues of 1,4-cyclohexanedimethanol.

In one embodiment, R" of said copolyester can be selected from residues of at least one of ethylene glycol, propylene glycol, 1,3-propanediol, and butanediol; alternatively, R" can be residues of ethylene glycol or 1,3-propanediol or combinations thereof.

In one embodiment, R' of the copolyester of the invention can comprise residues of at least one of the following: terephthalic acid, isophthalic acid, cyclohexane-1,4-dicarboxylic acid, furan-2,5-dicarboxylic acid, adipic acid, sebacic acid, or esters thereof or combinations thereof; alternatively, R' can comprise residues of at least one of the following: terephthalic acid, isophthalic acid, cyclohexane-1,4-dicarboxylic acid, furan-2,5-dicarboxylic acid or esters thereof or combinations thereof; and alternatively, R' can comprise residues of terephthalic acid or esters thereof or combinations thereof.

In one embodiment, the pentamer of the invention can contain substantially no active catalyst or no active catalyst. By "no active catalyst", it is meant that the pentamer itself is unreactive when exposed to conditions standard in the art for polymerization.

In one embodiment, the copolyester of this invention can have less than 10 mole % loss, or less than 9 mole %, or less than 8 mole % loss, or less than 7 mole % loss, or less than 6 mole % loss, or less than 5 mole % loss, or less than 4 mole % loss, or less than 3 mole % loss, or less than 2 mole % loss, or less than 1 mole % loss, or no loss of said R residues during polycondensation.

In certain embodiments, the polymer compositions of the invention can include copolyesters comprising residues of 70 to 100 mole % terephthalic acid, and optionally, 0.01 to 30 mole %, or 0.01 to 20 mole %, or 0.01 to 10 mole %, or 0.01 to 5 mole % of isophthalic acid, or esters thereof and/or mixtures thereof.

In certain embodiments, the polymer compositions of the invention can include copolyesters comprising 1,4-cyclohexanedimethanol and, optionally, ethylene glycol. In certain embodiments, the polymer compositions of the invention can include copolyesters comprising from 50 mole % to 100 mole %, or from 60 mole % to 100 mole %, or from 65 mole % to 100 mole %, or from 70 mole % to 100 mole %, or from 75 mole % to 100 mole %, or from 80 mole % to 100 mole %, or from 90 mole % from to 100 mole %, or 95 mole % to 100 mole %, of residues of 1,4-cyclohexanedimethanol and, optionally, from 0 mole % to 50 mole %, or from 0 mole % to 40 mole %, or from 0 mole % to 35 mole %, or from 0 mole % to 30 mole %, or from 0 mole % to 25 mole %, or from 0 mole % to 20 mole %, or from 0 mole % to 10 mole %, or from 0 mole % to 5 mole %, of residues of ethylene glycol.

In certain embodiments, the polymer compositions of the invention can include copolyesters comprising residues of 99 to 100 mole % terephthalic acid and residues of 99 to 100 mole % 1,4-cyclohexanedimethanol. In certain embodiments, the polyester comprises residues of diethylene glycol. In embodiments, the polyester comprises residues of terephthalic acid, isophthalic acid and 1,4-cyclohexanedimethanol. In embodiments, the polyester comprises from 50 mole % to 99.99 mole % of residues of 1,4-cyclohexanedimethanol, 0.01 mole % to 50 mole % of residues of ethylene glycol, and from 70 mole % to 100 mole % of residues of terephthalic acid. In embodiments, the polyester comprises from 80 mole % to 99.99 mole % of residues of 1,4-cyclohexanedimethanol and 0.01 mole % to 20 mole % of residues of ethylene glycol. In embodiments, the polyester comprises from 90 mole % to 99.99 mole % of residues of 1,4-cyclohexanedimethanol and 0.01 mole % to 10 mole % of residues of ethylene glycol. In embodiments, the polyester comprises from 95 mole % to 99.99 mole % of residues of 1,4-cyclohexanedimethanol and 0.01 mole % to 5 mole % of residues of ethylene glycol. In embodiments, the polyester comprises from 95 mole % to 99.99 mole % of residues of 1,4-cyclohexanedimethanol, 0.01 mole % to 10 mole % of residues of ethylene glycol, from 90 mole % to 100 mole % of residues of terephthalic acid, and 0.01 to 10 mole % of residues of isophthalic acid. In embodiments, the polyester comprises from 95 mole % to 100 mole % of residues of 1,4-cyclohexanedimethanol, 0.01 mole % to 5 mole % of residues of ethylene glycol, from 95 mole % to 100 mole % of residues of terephthalic acid, and 0.01 to 5 mole % of residues of isophthalic acid. In embodiments, the polyester consists essentially of residues of terephthalic acid or an ester thereof and 1,4-cyclohexanedimethanol. In embodiments, the polyester comprising consists essentially of residues of terephthalic acid or an ester thereof, 1,4-cyclohexanedimethanol and ethylene glycol. In embodiments, the polyester comprises 0 mole % to 30 mole % or 0 mole % to 20 mole % or 0 mole % to 10 mole % or 0 mole % to 5 mole % or 0.01 mole % to 30 mole % or 0.01 mole % to 20 mole % or 0.01 mole % to 10 mole % or 0.01 mole % to 5 mole % isophthalic acid residues, based on a total of 100 mole % acid residues and a total of 100 mole % of diol residues. In embodiments, the polyester comprises from 20 mole % to less than 50 mole % of residues of 1,4-cyclohexanedimethanol, greater than 50 mole % to 80 mole % of residues of ethylene glycol, and from 70 mole % to 100 mole % of residues of terephthalic acid. In embodiments, the polyester comprises from 20 mole % to 40 mole % of residues of 1,4-cyclohexanedimethanol, 60 mole % to 80 mole % of residues of ethylene glycol, and from 70 mole % to 100 mole % of residues of terephthalic acid. In embodiments, the polyester comprises from 25 mole % to 40 mole % of residues of 1,4-cyclohexanedimethanol, 60 mole % to 75 mole % of residues of ethylene glycol, and from 70 mole % to 100 mole % of residues of terephthalic acid. In embodiments, the polyester comprises from 25 mole % to 35 mole % of residues of 1,4-cyclohexanedimethanol, 65 mole % to 75 mole % of residues of ethylene glycol, and from 70 mole % to 100 mole % of residues of terephthalic acid. In embodiments, the polyester comprises 0 to 20 mole % of residues of 1,4-cyclohexanedimethanol and 80 to 100 of residues of ethylene glycol.

In certain embodiments, the polyester comprises residues of neopentyl glycol. In embodiments, the polyester comprises 2,2,4,4-cyclobutanediol-1-1,3-cyclobutanediol residues.

In embodiments, the polyester comprises from 0.01 to 99 mole % 2,2,4,4-tetramethyl-1,3-cyclobutanediol residues and from 0.01 to 99 mole % 1,4-cyclohexanedimethanol residues and 70 to 100 mole % terephthalic acid residues. In embodiments, the polyester comprises from 20 to 40 mole % 2,2,4,4-tetramethyl-1,3-cyclobutanediol residues, from 20 to 40 mole % 1,4-cyclohexanedimethanol residues, 20 to 60 mole % of ethylene glycol residues.

In embodiments, the polyester comprises from 0.01 to 15 mole % 2,2,4,4-tetramethyl-1,3-cyclobutanediol residues. In embodiments, the polyester comprises from 15 to 40 mole % 2,2,4,4-tetramethyl-1,3-cyclobutanediol residues and from 60 to 85 mole % 1,4-cyclohexanedimethanol residues. In embodiments, the polyester comprises from 20 to 40 mole % 2,2,4,4-tetramethyl-1,3-cyclobutanediol residues and from 60 to 80 mole % 1,4-cyclohexanedimethanol residues. In embodiments, the polyester comprises from 20 to 30 mole % 2,2,4,4-tetramethyl-1,3-cyclobutanediol residues and from 70 to 80 mole % 1,4-cyclohexanedimethanol residues and 70 to 100 mole % terephthalic acid residues. In embodiments, the polyester comprises from 30 to 40 mole % 2,2,4,4-tetramethyl-1,3-cyclobutanediol residues and from 60 to 70 mole % 1,4-cyclohexanedimethanol residues and 70 to 100 mole % terephthalic acid residues.

In certain embodiments, the polyester component comprises residues of 1,4-cyclohexanedicarboxylic acid or an ester thereof. In embodiments, the polyester component comprises residues of dimethyl-1,4-cyclohexanedicarboxylate. In embodiments, the polyester component comprises residues 1,4-cyclohexanedicarboxylic acid or an ester thereof in the amount of from 70 to 100 mole % or from 80 to 100 mole % or from 90 to 100 mole % or from 95 to 100 mole % or from 98 to 100 mole %, based on a total of 100 mole % acid residues and a total of 100 mole % diol residues.

In some aspects of the invention, the copolyesters useful in the invention may comprise a diacid component comprising at least 70 mole % of residues of terephthalic acid, isophthalic acid, or mixtures thereof; and a diol component comprising (a) the residues of 2,2,4,4-tetramethyl-1,3-cyclobutanediol and residues of 1,4-cyclohexanedimethanol (TMCD Copolyesters).

In one embodiment, the polyester can comprise from 0.01 to 99.99 mole % 2,2,4,4-tetramethyl-1,3-cyclobutanediol residues and 99.99 to 0.01 mole % 1,4-cyclohexanedimethanol residues, or from 20 to 50 mole % 2,2,4,4-tetramethyl-1,3-cyclobutanediol residues and 50 to 80 mole % 1,4-cyclohexanedimethanol residues, or from 20 to less than 50 mole % 2,2,4,4-tetramethyl-1,3-cyclobutanediol residues and greater than 50 to 80 mole % 1,4-cyclohexanedimethanol residues, or from 15 to 40 mole % 2,2,4,4-tetramethyl-1,3-cyclobutanediol residues and 60 to 85 mole % 1,4-cyclohexanedimethanol residues, or from 20 to 40 mole % 2,2,4,4-tetramethyl-1,3-cyclobutanediol residues and 60 to 80 mole % 1,4-cyclohexanedimethanol residues, or from 20 to 30 mole % 2,2,4,4-tetramethyl-1,3-cyclobutanediol residues and 70 to 80 mole % 1,4-cyclohexanedimethanol residues, or from 30 to 40 mole % 2,2,4,4-tetramethyl-1,3-cyclobutanediol residues and 60 to 70 mole % 1,4-cyclohexanedimethanol residues, or from 0.01 to 15 mole % 2,2,4,4-tetramethyl-1,3-cyclobutanediol residues and 85 to 99.99 mole % 1,4-cyclohexanedimethanol residues, or from 20 to 40 mole % 2,2,4,4-tetramethyl-1,3-cyclobutanediol residues, from 20 to 40 mole % 1,4-cyclohexanedimethanol residues and 20 to 60 mole % of ethylene glycol residues, and, for all of these ranges, optionally, 70 to 100 mole % terephthalic acid or isophthalic residues or mixtures thereof, based on a total of 100 mole % acid residues and a total of 100 mole % diol residues.

In one embodiment, the polyester can comprise 20 to 40 mole % 2,2,4,4-tetramethyl-1,3-cyclobutanediol residues and 60 to 80 mole % 1,4-cyclohexanedimethanol residues and 70 to 100 mole % terephthalic acid residues, based on a total of 100 mole % acid residues and a total of 100 mole % diol residues.

In certain embodiments, the polymer compositions of the invention may can include copolyesters comprising, optionally, 0.01 to 30 mole %, or 0.01 to 20 mole %, or 0.01 to 10 mole %, or 0.01 to 5 mole % of terephalic acid and/or isophthalic acid, or esters thereof and/or mixtures thereof; and a diol component comprising: (a) from 20 to less than 50 mole % of 1,4-cyclohexanedimethanol and residues from greater than 50 to 80 mole % ethylene glycol residues; or from 20 to 40 mole % of 1,4-cyclohexanedimethanol residues and from 60 to 80 mole % ethylene glycol residues, or from 20 to 40 mole % of 1,4-cyclohexanedimethanol residues and from 60 to 80 mole % ethylene glycol residues, or from 25 to 40 mole % of 1,4-cyclohexanedimethanol residues and from 60 to 75 mole % ethylene glycol residues, or from 25 to 35 mole % of 1,4-cyclohexanedimethanol residues and from 65 to 75 mole % ethylene glycol residues (PETG); or (b) from 50 mole % to 99.99 mole %, or from 55 mole % to 99.99 mole %, or from 60 mole % to 99.99 mole %, or from 65 mole % to 99.99 mole %, or from 70 mole % to 99.99 mole %, or from 75 mole % to 99.99 mole %, or from 80 mole % to 99.99 mole %, or from 85 mole % to 99.99 mole % percent, or from 90 mole % from to 99.99 mole %, or 95 mole % to 99.99 mole %, of residues of 1,4-cyclohexanedimethanol and from 0.01 mole % to 50 mole %, or from 0.01 mole % to 45 mole %, or from 0.01 mole % to 40 mole %, or from 0.01 mole % to 35 mole %, or from 0.01 mole % to 30 mole %, or from 0.01 mole % to 25 mole %, or from 0.01 mole % to 20 mole %, or from 0.01 mole % to 15 mole %, or from 0.01 mole % to 10 mole %, or from 0.01 mole % to 5 mole %, of residues of ethylene glycol (PCTG); or (c) from 95 to 99.99 mole %, of residues of 1,4-cyclohexanedimethanol and from 0.01 to 10 mole % or from 0.01 to 5 mole % of residues of isophthalic acid, and from 0.01 to 10 mole % or from 0.01 to 5 mole % of residues of ethylene glycol (PCTA) or (d) 0 to 20 mole % of residues of 1,4-cyclohexanedimethanol and 80 to 100 mole % of residues of ethylene glycol (PET or glycol modified PET) or (e) isosorbide polymers comprising 1,4-cyclohexanedimethanol and optionally, ethylene glycol or (f) isosorbide polymers comprising ethylene glycol or (g) (PCT as defined herein). In certain embodiments, the diol component can comprise from 10 mole % to 40 mole %, or from 15 mole % to 35 mole %, or from 20 mole % to 35 mole %, or from 20 mole % to 30 mole %, or from 20 mole % to 40 mole %, or from 20 mole % to 35 mole %, of residues of isosorbide; from 30 mole % to 70 mole %, or from 40 mole % to 70 mole %, or from 45 mole % to 65 mole %, or from 45 mole % to 60 mole %, or from 45 mole % to 55 mole %, or from 47 mole % to 65 mole %, or from 48 mole % from to 65 mole %, or 49 mole % to 65 mole %, or 50 mole % to 65 mole %, or from 47 mole % to 60 mole %, or from 48 mole % from to 60 mole %, or 49 mole % to 60 mole %, or 50 mole % to 60 mole %, of residues of 1,4-cyclohexanedimethanol and, optionally, from 0 mole % to 40 mole %, or from 0 mole % to 35 mole %, or from 0 mole % to 30 mole %, or from 0 mole % to 25 mole %, or from 0 mole % to 20 mole %, or from 0 mole % to 15 mole %, or from 0 mole % to 10 mole %, or from 0 mole % to 5 mole %, of residues of ethylene glycol. In one embodiment, the diol component can comprise from 18 mole % to 35 mole %, or from 20 mole % to 35 mole %, of residues of isosorbide; from 40 mole % to 58 mole %, or from 45 mole % to 55 mole %, of residues of 1,4-cyclohexanedimethanol; and, from 15 mole % to 25 mole %, or from 20 mole % to 25 mole %, of residues of ethylene glycol.

In one embodiment, the copolyester of the invention can comprise 70 to 100 mole % terephthalic acid residues and 0 to 30 mole % isophthalic acid residues, or 80 to 100 mole % terephthalic acid residues and 0 to 20 mole % isophthalic acid residues, wherein the total mole % of diacid residues equals 100 mole % and the total mole % of diol residues equals 100 weight %.

In one embodiment, the copolyester of this invention can comprise diol residues comprising from 20 to 100 mole % of 1,4-cyclohexanedimethanol residues and 0 to 100 mole % of ethylene glycol residues, or from 20 to 40 mole % of 1,4-cyclohexanedimethanol residues and 60 to 80 mole % of ethylene glycol residues.

In one embodiment, the copolyester can comprise diol residues from about 20 to 45 mole % 2,2,4,4-tetramethyl-1,3-cyclobutanediol residues, from 55 to about 80 mole % of 1,4-cyclohexanedimethanol residues, and from 0 to 100 mole % of ethylene glycol residues; in one embodiment, the copolyester of the invention can comprise diol residues comprising from about 20 to 30 mole % 2,2,4,4-tetramethyl-1,3-cyclobutanediol residues, from 70 to about 80 mole % of 1,4-cyclohexanedimethanol residues, and from 0 to 100 mole % of ethylene glycol residues; and in one embodiment, the copolyester of the invention can comprise diol residues comprising from about 30 to 40 mole % 2,2,4,4-tetramethyl-1,3-cyclobutanediol residues, from 60 to about 70 mole % of 1,4-cyclohexanedimethanol residues, and from 0 to 100 mole % of ethylene glycol residues.

In one embodiment, the copolyesters of the invention can comprise diol residues comprising from about 0 to 20 mole % ethylene glycol residues and from about 0 to 100 mole % of 1,4-cyclohexanedimethanol (CHDM) residues.

In one embodiment, the copolyester of the invention can comprise from about 10 to 45 mole % 2,2,4,4-tetramethyl-1,3-cyclobutanediol residues, from about 55 to 90 mole % of ethylene glycol residues, and from about 0 to 100 mole % of 1,4-cyclohexanedimethanol residues.

In one embodiment, the copolyester of the invention can comprise diol residues comprising from about 15 to 30 mole % 2,2,4,4-tetramethyl-1,3-cyclobutanediol residues, from about 55 to 90 mole % of ethylene glycol residues, and from about 0 to 100 mole % of 1,4-cyclohexanedimethanol residues.

In one embodiment, the copolyester of the in invention can contain contains no residues of 1,4-cyclohexanedimethanol.

In one embodiment, this invention provides at least one diester intermediate comprising the following structure:

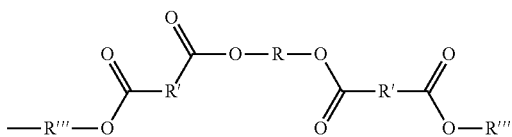

wherein R comprises residues of at least one diol;
wherein R''' comprises at least one of methyl, ethyl, t-butyl, or benzyl, or mixtures thereof; and
wherein R' comprises residues of at least one diacid or diester.

In one embodiment, this invention provides at least one diester wherein said diol is selected from residues of 2,2,4,4-tetramethylcyclobutane-1,3-diol, 2,2-dimethyl-1,3-propanediol, 1,2-cyclohexanedimethanol, 1,3-cyclohexanedimethanol, 1,4-cyclohexanedimethanol, 2,2,4-trimethyl-1,3-pentanediol, hydroxypivalyl hydroxypivalate, 2-methyl-1,3-propanediol, 2-butyl-2-ethyl-1,3-propanediol, 1,4-butanediol, 1,3-propanediol, 1,5-pentanediol, 1,6-hexanediol, ethylene glycol, diethylene glycol, triethylene glycol, isosorbide, 1,6-hexanediol, 3-methyl-pentanediol, 2-methylpentanediol, 2,2,4-tri-methylpentane-diol, 2-ethylhexanediol, 2,2-diethylpropanediol, 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, or 2,2-bis-(4-hydroxypropoxyphenyl)-propane.

In one embodiment, the diester intermediate of this invention is provided wherein R is selected from residues of at least one of 2,2,4,4-tetramethylcyclobutane-1,3-diol, 2,2-dimethyl-1,3-propanediol, 1,4-cyclohexanedimethanol, ethylene glycol, propylene glycol, 1,3-propanediol, and butanediol; alternatively, R can be selected from residues of at least one of 2,2,4,4-tetramethylcyclobutane-1,3-diol and 1,4-cyclohexanedimethanl; alternatively, R can be selected from residues of 2,2,4,4-tetramethylcyclobutane-1,3-diol; or alternatively, R is selected from residues of 1,4-cyclohexanedimethanol.

In one embodiment, the diester intermediate of this invention can comprise the following structure:

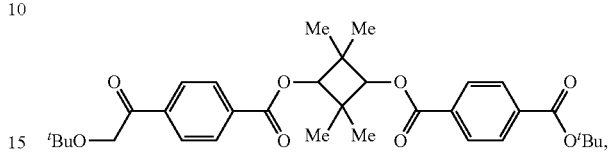

otherwise known as di-tert-butyl O,O'-(2,2,4,4-tetramethylcyclobutane-1,3-diyl)diterephthalate.

In one embodiment, the diester intermediate of this invention can comprise the following structure:

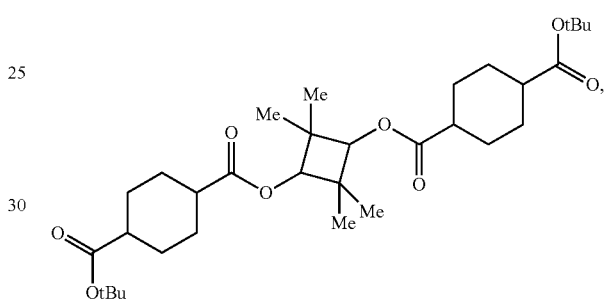

otherwise known as 4,4'-di-tert-butyl O'1,O1-(2,2,4,4-tetramethylcyclobutane-1,3-diyl)bis(cyclohexane-1,4-dicarboxylate).

In one embodiment, the diester intermediate of this invention can comprise the following structure:

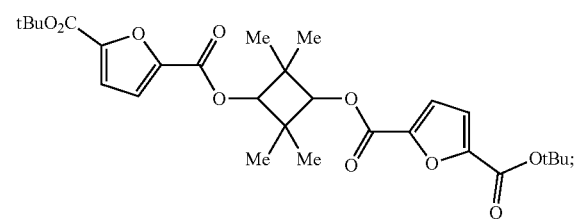 [SMILES: CC(C)(C)OC(=O)c1ccc(C(=O)OC2C(C)(C)C(OC(=O)c3ccc(C(=O)OC(C)(C)C)o3)C2(C)C)o1]

otherwise known as 5,5'-di-tert-butyl O'2,O2-(2,2,4,4-tetramethylcyclobutane-1,3-diyl)bis(furan-2,5-dicarboxylate)

In one embodiment, the diester intermediate of this invention can comprise the following structure:

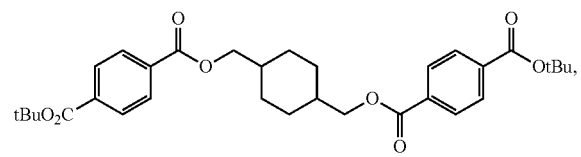 [SMILES: CC(C)(C)OC(=O)c1ccc(C(=O)OCC2CCC(COC(=O)c3ccc(C(=O)OC(C)(C)C)cc3)CC2)cc1]

otherwise known as di-tert-butyl O,O'-(cyclohexane-1,4-diylbis(methylene)diterephthalate] tetramethylcyclobutane-1,3-diyl)bis(furan-2,5-dicarboxylate).

In one embodiment, the diester intermediate of this invention can comprise the following structure:

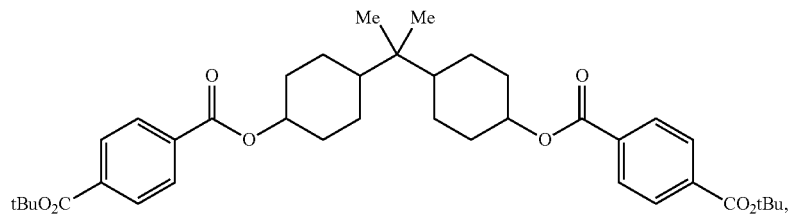 [SMILES: CC(C)(C)OC(=O)c1ccc(C(=O)OC2CCC(C(C)(C)C3CCC(OC(=O)c4ccc(C(=O)OC(C)(C)C)cc4)CC3)CC2)cc1]

otherwise known as di-tert-butyl O,O'-(propane-2,2-diylbis (cyclohexane-4,1-diyl))diterephthalate.

In one embodiment, the diester intermediate of this invention can comprise the following structure:

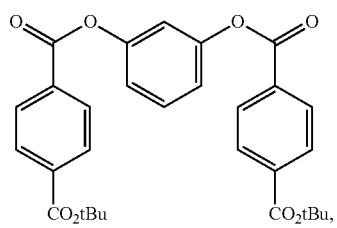 [SMILES: CC(C)(C)OC(=O)c1ccc(C(=O)Oc2cccc(OC(=O)c3ccc(C(=O)OC(C)(C)C)cc3)c2)cc1]

otherwise known as O,O'-(1,3-phenylene)di-tert-butyl diterephthalate.

In one embodiment, the diacid of this invention can comprise the following structure:

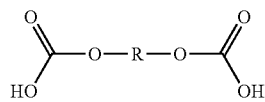

wherein said diol is selected from residues of 2,2,4,4-tetramethylcyclobutane-1,3-diol, 2,2-dimethyl-1,3-propanediol, 1,2-cyclohexanedimethanol, 1,3-cyclohexanedimethanol, 1,4-cyclohexanedimethanol, 2,2,4-trimethyl-1,3-pentanediol, hydroxypivalyl hydroxypivalate, 2-methyl-1,3-propanediol, 2-butyl-2-ethyl-1,3-propanediol, 1,4-butanediol, 1,3-propanediol, 1,5-pentanediol, 1,6-hexanediol, ethylene glycol, diethylene glycol, triethylene glycol, isosorbide, 1,6-hexanediol, 3-methyl-pentanediol, 2-methylpentanediol, 2,2,4-tri-methylpentane-diol, 2-ethylhexanediol, 2,2-diethylpropanediol, 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, or 2,2-bis-(4-hydroxypropoxyphenyl)-propane.

The diacid of this invention is provided wherein R can be selected from residues of at least one of 2,2,4,4-tetramethylcyclobutane-1,3-diol, 2,2-dimethyl-1,3-propanediol, 1,4-cyclohexanedimethanol, ethylene glycol, propylene glycol, 1,3-propanediol, and butanediol; alternatively, R can be selected from residues of at least one of 2,2,4,4-tetramethylcyclobutane-1,3-diol and 1,4-cyclohexanedimethanol; alternatively, R can be selected from residues of 2,2,4,4-tetramethylcyclobutane-1,3-diol; and alternatively, R can be selected from residues of 1,4-cyclohexanedimethanol.

Examples of the diacid of this invention include but are not limited to 4,4'-(2,2,4,4-tetramethylcyclobutane-1,3-diyl) bis(oxy)bis(carbonyl)dibenzoic acid, 4,4'-(cyclohexane-1,4-diylbis(methylene)bis(oxy)bis(carbonyl)dibenzoic acid; 4,4'-(propane-2,2-diylbis(cyclohexane-4,1-diyl)bis(oxy)bis (carbonyl)dibenzoic acid); and 4,4'-(1,3-phenylenebis(oxy) bis(carbonyl)dibenzoic acid.

In one embodiment, at least one diacid of this invention can be 4,4'-(2,2,4,4-tetramethylcyclobutane-1,3-diyl)bis (oxy)bis(carbonyl)dibenzoic acid.

In one embodiment, the diacids of this invention can be used to make the diester intermediates of this invention.

In one embodiment, the diester intermediates of the invention can be used to make the pentamers of the invention.

In one embodiment, the pentamers of this invention can be used to make any copolyester of the invention using polycondensation.

In one embodiment, this invention also provides a process for making a polycondensation pre-copolyester, a copolyester, and/or other copolyester precursors, comprising the following steps:

A. Acylation of at least one diacid chloride with at least one alcohol to form at least one diester;
B. Partial hydrolysis of the diester product of Step A to form at least one monoacid;
C. Esterifying the monoacid of Step B with at least one diol to form a diester;
D. Reacting the diester of Step C under acidic conditions to form a diacid; and subsequently, performing either Step E or Step F as follows:
E. Bisalkylation of the diacid of Step D with at least one haloalcohol to form a pentamer, or
F. Esterifiying the diacid of Step D under esterification conditions with at least one diol to form a pentamer, provided that the diol is not the same as the diol used in Step C.

In one embodiment, the invention provides a process for making a polycondensation pre-polyester, a polyester, or both, comprising the following steps:

A. Acylation of at least one diacid chloride to form at least one diester, comprising the following steps:
  1. Adding at least one alcohol, adding at least one base, and optionally, at least one aprotic solvent to a first reaction zone;
  2. Adding at least one aprotic solvent and at least one diacid chloride to a second reaction zone;
  3. Feeding the contents in the first reaction zone into the second reaction zone;
B. Partial hydrolysis of the diester product of Step A to form at least one monoacid comprising the following steps:
  1. adding the product of Step A and at least one aprotic solvent to a third reaction zone;
  2. adding at least one base, water, and at least one alcohol to a fourth reaction zone;

3. Feeding the contents in the fourth reaction zone into the third reaction zone; and C. Esterifying the monoacid of Step B to form a diester comprising the following steps:

D. Add the monoacid of Step B, at least one diol, at least one catalyst (e.g., 4-dimethylaminopyridine), at least one aprotic solvent and at least one carbodiimide and react under esterification conditions; Reacting the diester of Step C under acidic conditions to form a diacid, comprising the following steps:

1. Reacting the diester of Step C with at least one acid, for example, a Lewis acid such as iodine, and at least one aprotic solvent; and then performing either Step E or Step F as follows:

E. Bisalkylation of the diacid of Step D to form a pentamer comprising the following step: dissolve the diacid of Step D in at least one aprotic solvent, add at least one base, and then react with at least one haloalcohol;

F: Esterifiying the diacid of Step D to form a pentamer comprising the following step: dissolve the diacid of Step D in at least one aprotic solvent and react with at least one diol and at least one carbodiimide with at least one catalyst (e.g., 4-dimethylaminopyridine), provided that the diol is not the same as in Step C.

In Step A of the process of this invention, at least one diacid chloride can be selected from the group consisting of terephthaloyl chloride, isophthaloyl chloride, cyclohexane-1,4-dicarbonyl chloride, furan-2,5-dicarbonyl chloride, adipoyl chloride, and sebacoyl chloride. In one embodiment, at least one diacid chloride can be used and can be selected from terephthaloyl chloride, cyclohexane-1,4-dicarbonyl chloride, and furan-2,5-dicarbonyl chloride.

In one embodiment, the alcohol of Step A(1) of the process of the invention can be selected from the group consisting of tert-butanol, methanol, ethanol and benzyl alcohol.

In one embodiment, the base of Step A(1) is at least one base can be selected from pyridine, (such as 4-dimethylaminopyridine), triethylamine, diisopropylethylamine.

In one embodiment, the aprotic solvent of Steps A(1) and (2) can be selected from the group consisting of methylene chloride, hexane, benzene, toluene, 1,4-dioxane, chloroform, diethyl ether, dichloromethane, N-methylpyrrolidone, tetrahydrofuran, ethyl acetate, acetone, dimethylformamide, acetonitrile, and dimethyl sulfoxide; in one embodiment, the aprotic solvent of Steps A (1) and (2) is methylene chloride.

In one embodiment, subsequent to Step A (3) of the process of the invention, and after the reaction goes below the reflux temperature, the temperature can be adjusted to 30 to 50° C. and can be held for about 5-15 hours under continuous stirring.

In one embodiment, the diester product of Step A can be any diester of the invention, for example, 1,4-di-tert-butyl terephthalate diester.

In one embodiment, the aprotic solvent of Step B (1) and (2) of the process of the invention which can include but is not limited to methylene chloride, toluene, tetrahydrofuran, acetonitrile, dioxane, or acetone; in one embodiment, the aprotic solvent of Step B(1) can be toluene.

In one embodiment, the base of Step B(2) of the process of the invention can be selected from potassium hydroxide or sodium hydroxide; in one embodiment, the base of Step B(2) can be potassium hydroxide.

In one embodiment, the alcohol of Step B is selected from the group consisting of tert-butanol, methanol, ethanol and benzyl alcohol; in one embodiment, the alcohol of Step B can be methanol.

In one embodiment, the at least one monoacid of Steps B and C can be selected from 4-tert-butoxycarbonyl)benzoic acid, 4-(tert-butoxycarbonyl)cyclohexane-1-carboxylic acid), or 5-(tert-butoxycarbonyl)furan-2-carboxylic acid, tert-methoxycarbonyl)benzoic acid, 4-(tert-methoxycarbonyl)cyclohexane-1-carboxylic acid), or 5-(tert-methoxycarbonyl)furan-2-carboxylic acid, tert-ethoxycarbonyl)benzoic acid, 4-(tert-ethoxycarbonyl)cyclohexane-1-carboxylic acid), or 5-(tert-ethoxycarbonyl)furan-2-carboxylic acid, tert-benzyloxycarbonyl)benzoic acid, 4-(tert-benzyloxycarbonyl)cyclohexane-1-carboxylic acid), or 5-(tert-benzyloxycarbonyl)furan-2-carboxylic acid; in one embodiment, the at least one monoacid of Steps B and C is 4-tert-butoxycarbonyl)benzoic acid.

In one embodiment, the diol of Step C of the process of the invention can be selected from residues of at least one diol as follows: 2,2,4,4-tetramethylcyclobutane-1,3-diol, 2,2-dimethyl-1,3-propanediol, 1,2-cyclohexanedimethanol, 1,3-cyclohexanedimethanol, 1,4-cyclohexanedimethanol, 2,2,4-trimethyl-1,3-pentanediol, hydroxypivalyl hydroxypivalate, 2-methyl-1,3-propanediol, 2-butyl-2-ethyl-1,3-propanediol, 1,4-butanediol, 1,3-propanediol, 1,5-pentanediol, 1,6-hexanediol, ethylene glycol, diethylene glycol, triethylene glycol, isosorbide, 1,6-hexanediol, 3-methyl-pentanediol, 2-methylpentanediol, 2,2,4-tri-methylpentane-diol, 2-ethylhexanediol, 2,2-diethylpropanediol, 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, resorcinol, 4,4'-(propane-2,2-diyl)dicyclohexanol, or 2,2-bis-(4-hydroxypropoxyphenyl)-propane; in one embodiment, the diol of Step C can be selected from at least one of 2,2,4,4-tetramethylcyclobutane-1,3-diol, 2,2-dimethyl-1,3-propanediol, 1,4-cyclohexanedimethanol, ethylene glycol, propylene glycol, 1,3-propanediol, butanediol., resorcinol or 4,4'-(propane-2,2-diyl) dicyclohexanol; in one embodiment, at least one diol of Step C can be 2,2,4,4-tetramethylcyclobutane-1,3-diol; in one embodiment, at least one diol of Step C can be 1,4-cyclohexanedimethanol; in one embodiment, diols of Step C can be selected from at least one of 2,2,4,4-tetramethylcyclobutane-1,3-diol and 1,4-cyclohexanedimethanol; in one embodiment, diols of Step C can be selected from at least one of 2,2,4,4-tetramethylcyclobutane-1,3-diol and ethylene glycol; in one embodiment, the diols of Step C can be selected from at least one of 2,2,4,4-tetramethylcyclobutane-1,3-diol, 1,4-cycohexanedimethanol and ethylene glycol; in one embodiment, the diols of Step C can be selected from at least one of 1,4-cycloehexanedimethanol and ethylene glycol in one embodiment, the diols of Step C can be selected from at least one of ethylene glycol, propylene glycol, 1,3-propanediol, or butanediol; in one embodiment, at least one diol of Step C can be ethylene glycol.

In one embodiment, at least one carbodiimide of Step C of the process of the invention can be selected from diisopropylcarbodiimide and dicyclohexylcarbodiimide; in one embodiment, the carbodiimide of Step C can be diisopropylcarbodiimide.

In one embodiment, the aprotic solvent of Step C of the process of the invention can be selected from methylene chloride or dimethylformamide; in one embodiment, the aprotic solvent of Step C is methylene chloride.

In one embodiment, the aprotic solvent of Step D of the process of the invention can be acetonitrile.

In one embodiment, the diacid product of Step D is selected from 4,4'-(2,2,4,4-tetramethylcyclobutane-1,3-diyl)bis(oxy)bis(carbonyl)dibenzoic acid, 4,4'-(cyclohexane-1,4-diylbis(methylene)bis(oxy)bis(carbonyl)dibenzoic acid; 4,4'-(propane-2,2-diylbis(cyclohexane-4,1-diyl)bis(oxy)bis(carbonyl)dibenzoic acid); and 4,4'-(1,3-phenylenebis(oxy)bis(carbonyl)dibenzoic acid; in one embodiment, the diacid product of Step D can be 4,4'-(2,2,4,4-tetramethylcyclobutane-1,3-diyl)bis(oxy)bis(carbonyl)dibenzoic acid.

In one embodiment, the polycondensation prepolyester of Step D of the process of the invention can be selected from [bis(2-hydroxyethyl) O,O'-(2,2,4,4-tetramethylcyclobutane-1,3-diyl)diterephthalate; 4,4'-bis(2-hydroxyethyl) O'11,O1-(2,2,4,4-tetramethylcyclobutane-1,3-diyl)bis(cyclohexane-1,4-dicarboxylate); 5,5'-bis(2-hydroxyethyl) O'2,O2-(2,2,4,4-tetramethylcyclobutane-1,3-diyl) bis(furan-2,5-dicarboxylate); O,O'-(cyclohexane-1,4-diylbis(methylene)bis(2-hydroxyethyl)diterephthalate); and bis(2-hydroxyethyl) O,O'-(propane-2,2-diyl-bis(cyclohexane-4,1-diyl)diterephthalate).

In one embodiment, the process of the invention also comprises Step E: dissolving the diacid of Step D of the process of the invention in at least one aprotic solvent, adding at least one base, and then reacting with at least one haloalcohol.

In one embodiment, at least one base of Step E of the process of the invention can be selected from potassium carbonate, sodium carbonate, or cesium carbonate; in one embodiment, at least one base of Step E can be potassium carbonate.

In one embodiment, at least one haloalcohol of Step E of the process of the invention can be selected from a bromoalcohol or a chloroalcohol.

In one embodiment, at least one haloalcohol of Step E of the process of the invention can be selected from 2-bromoethanol, 3-bromopropanol, 4-bromobutanol, 5-bromopentanol, 6-bromohexanol, 2-chloroethanol, 3-chloropropanol, 4-chlorobutanol, 5-chloropentanol, or 6-chlorohexanol; in one embodiment, at least one haloalcohol can be 2-bromoethanol.

In one embodiment, the aprotic solvent of Step F of the process of the invention can be dimethylformamide.

In one embodiment, at least one carbodiimide of Step F of the process of the invention can be selected from diisopropylcarbodiimide and dicyclohexylcarbodiimide; in one embodiment, the carbodiimide of Step F can be diisopropylcarbodiimide.

In one embodiment, the diol of Step F of the process of the invention can be the same as those of Step C of the process of the invention.

In one embodiment, the reaction mixture can be allowed to stir at room temperature for 5 to 20 (12) hours.

In one embodiment, this invention provides at least one trimer or at least one pentamer formed using any of the processes of the invention. These trimers and pentamers can include but are not limited to any of those herein.

In one embodiment, at least one pentamer made from the process of the invention can include but are not limited to [bis(2-hydroxyethyl) O,O'-(2,2,4,4-tetramethylcyclobutane-1,3-diyl)diterephthalate; 4,4'-bis(2-hydroxyethyl) O'1,O1-(2,2,4,4-tetramethylcyclobutane-1,3-diyl)bis(cyclohexane-1,4-dicarboxylate); 5,5'-bis(2-hydroxyethyl) O'2,O2-(2,2,4,4-tetramethylcyclobutane-1,3-diyl)bis(furan-2,5-dicarboxylate); O,O'-(cyclohexane-1,4-diylbis(methylene)bis(2-hydroxyethyl)diterephthalate); bis(2-hydroxyethyl) O,O'-(propane-2,2-diyl-bis(cyclohexane-4,1-diyl)diterephthalate), and O,O'-(1,3-phenylene)bis(2-hydroxyethyl)diterephthalate), in one embodiment, the pentamer can be O,O'-(1,3-phenylene)bis(2-hydroxyethyl)diterephthalate).

In one embodiment, at least one copolyester can be prepared according to any of the processes of the invention. This copolyester can comprise perfectly alternating repeat units of diol residues as defined herein. This copolyester can be made from at least one pentamer of the invention and comprise perfectly alternating repeat units of diols residues. Copolyester compositions of this invention can also be prepared using the copolyesters of the invention.

In one embodiment, at least one copolyester of the invention can be prepared according to any process or process steps described herein or otherwise known in the art to be chemically equivalent. In one embodiment, at least one of the polyester precursors of the invention, (e.g. pentamers) can be prepared according to any process or process steps described herein or otherwise known in the art to be chemically equivalent. Any of the steps of the processes of the invention can be substituted with other steps known in the art as long as the pentamers and copolyesters of the present invention are made. For example, one could use Steps A-C of the process of the invention and then use other process steps that are either chemically equivalent or produce different intermediate molecules such that the pentamer(s) of the present invention and copolyesters derived therefrom are the end result. Each step of the process of this invention is considered to be part of this invention as well as the combination of steps set forth herein.

Novel diester intermediates, monoacids, and diacids can be formed using the processes of the invention. These novel diester intermediates, monoacids, and/or diacids can be used to make the copolyesters of the invention.

In one embodiment, the catalysts useful in the invention can be any that are effective for polycondensation of the R" diol useful in the invention.

In one embodiment, the catalysts useful in the invention can be any one or more of titanium tetrachloride, manganese diacetate, antimony oxide, dibutyl tin diacetate, zinc chloride, germanium oxide and gallium oxide or derivatives thereof.

In one embodiment, the processes of the invention can employ the use of catalysts including but not limited to at least one of germanium, titanium, antimony and gallium, or combinations thereof or derivatives thereof.

In one embodiment, the copolyester compositions of the invention can include germanium, antimony and gallium or combinations thereof or derivatives thereof.

In one embodiment, the copolyester compositions of the invention can include germanium and antimony.

In one embodiment, there can be less than 10 mole % loss, or less than 9 mole % loss, or less than 8 mole % loss, or less than 7 mole % loss, or less than 6 mole %, or less than 5 mole % loss of the diol residues of Step C during polymerization.

For embodiments of the invention, the copolyesters of the invention can exhibit at least one of the following inherent viscosities as determined in 60/40 (wt/wt) phenol/tetrachloroethane at a concentration of 0.25 g/50 ml at 25° C.: 0.10 to 0.50 dL/g; 0.10 to 0.40 dL/g; 0.15 to 0.35 dL/g; 0.15 to 0.30 dL/g; 0.50 to 1.2 dL/g; 0.50 to 1.0 dL/g; 0.50 to 0.90 dL/g; 0.50 to 0.80 dL/g; 0.55 to 0.80 dL/g; 0.60 to 0.80 dL/g; 0.65 to 0.80 dL/g; 0.70 to 0.80 dL/g; 0.50 to 0.75 dL/g; 0.55 to 0.75 dL/g; or 0.60 to 0.75 dL/g.

The invention further relates to a polymer blend. The blend comprises:
  (a) 5 to 95 weight % of at least one of the copolyesters described above; and (b) 5 to 95 weight % of at least one of the polymeric components.

Suitable examples of the polymers that can be blended with the copolyesters of the invention include, but are not limited to, nylon, other polyesters different from those described herein, nylon, polyamides such as ZYTEL® from DuPont; copolyesters different from those described herein; polystyrene, polystyrene copolymers, styrene acrylonitrile copolymers, acrylonitrile butadiene styrene copolymers, poly(methylmethacrylate), acrylic copolymers, poly(ether-imides) such as ULTEM® (a poly(ether-imide) from General Electric); polyphenylene oxides such as poly(2,6-dimethylphenylene oxide) or poly(phenylene oxide)/polystyrene blends such as NORYL 1000® (a blend of poly(2,6-dimethylphenylene oxide) and polystyrene resins from General Electric); other polyesters; polyphenylene sulfides; polyphenylene sulfide/sulfones; poly(ester-carbonates); polycarbonates such as LEXAN® (a polycarbonate from General Electric); polysulfones; polysulfone ethers; and poly(ether-ketones) of aromatic dihydroxy compounds or mixtures of any of the other foregoing polymers.

The blends can be prepared by conventional processing techniques known in the art, such as melt blending or solution blending. In one embodiment, polycarbonate is not present in the polyester composition. If polycarbonate is used in a blend in the polyester compositions useful in the invention, the blends can be visually clear. However, the polyester compositions useful in the invention also contemplate the exclusion of polycarbonate as well as the inclusion of polycarbonate.

In certain embodiments for the polymer blend, the at least one other polymer is present in the blend in the amount of 50 weight % or less, or 40 weight % or less, or 30 weight % or less, or 20 weight % or less, or 10 weight % or less, or 5 weight % or less, based on the total weight of the blend equaling 100 weight %. In embodiments, the at least one other polymer is present in the polymer blend in the amount of 0.01 to 50 weight %, or 1 to 50 weight %, or 5 to 50 weight %, or 0.01 to 40 weight %, or 0.01 to 30 weight % or 0.01 to 20 weight %, or 0.01 to 10 weight % or 0.01 to 5 weight %, based on the total weight of the blend equaling 100 weight %.

In embodiments of the invention, the condensation copolyester comprises residues of a branching agent. In embodiments, the copolyester comprises 0.01 to 5 mole % or 0.01 to 4 mole % or from 0.01 to 3 mole % or from 0.01 to 2 mole % or from 0.01 to about 1.5 mole % or from 0.01 to 1 mole % or from 0.1 to 5 mole % or 0.1 to 4 mole % or from 0.1 to 3 mole % or from 0.1 to 2 mole % or from 0.1 to about 1.5 mole % or from 0.1 to 1 mole or from 0.5 to 5 mole % or 0.5 to 4 mole % or from 0.5 to 3 mole % or from 0.5 to 2 mole % or from 0.5 to about 1.5 mole % or from 0.5 to 1 mole % or from 1 to 5 mole % or 1 to 4 mole % or from 1 to 3 mole % or from 1 to 2 mole % of at least one branching agent or at least one polyfunctional branching agent, based on a total of 100 mole % acid residues and a total of 100 mole % diol residues. In embodiments, the polyfunctional branching agent has at least 3 carboxyl or hydroxyl groups. In embodiments, the polyfunctional branching agent comprises residues of trimellitic acid, trimellitic anhydride, trimesic acid, trimethyol ethane, trimethyolpropane, pentaerythritol, glycerine, tetra-maleaic anhydride, and trimer acid. In embodiments, the polyfunctional branching agent comprises residues of trimellitic anhydride, trimethyolpropane, pentaerythritol, glycerine, tetra-maleaic anhydride.

In other aspects of the invention, the Tg of the copolyesters useful in the invention can be, but is not limited to, at least one of the following ranges: −50 to 150° C.; −10 to 130° C.; −10 to 125° C.; −10 to 120° C.; −10 to 115° C.; −10 to 110° C.; −10 to 105° C.; −10 to 70° C.; −10 to 65° C.; −10 to 60° C.; −10 to 55° C.; −10 to 50° C.; −10 to 45° C.; −10 to 40° C.; −10 to 35° C.; −10 to 30° C.; −10 to 25° C.; −10 to 20° C.; −10 to 15° C.; −5 to 130° C.; −5 to 125° C.; −5 to 120° C.; −5 to 115° C.; −5 to 110° C.; −5 to 105° C.; −5 to 70° C.; −5 to 65° C.; −5 to 60° C.; −5 to 55° C.; −5 to 50° C.; −5 to 45° C.; −5 to 40° C.; −5 to 35° C.; −5 to 30° C.; −5 to 25° C.; −5 to 20° C.; −5 to 15° C.; 60 to 130° C.; 60 to 125° C.; 60 to 120° C.; 60 to 115° C.; 60 to 110° C.; 60 to 105° C.; 60 to 100° C.; 60 to 95° C.; 65 to 130° C.; 65 to 125° C.; 65 to 120° C.; 65 to 115° C.; 65 to 110° C.; 65 to 105° C.; 65 to 100° C.; 65 to 95° C.; 70 to 130° C.; 70 to 125° C.; 70 to 120° C.; 70 to 115° C.; 70 to 110° C.; 70 to 105° C.; 75 to 130° C.; 75 to 125° C.; 75 to 120° C.; 75 to 115° C.; 75 to 110° C.; 75 to 105° C.; 85 to 130° C.; 85 to 125° C.;

85 to 120° C.; 85 to 115° C.; 85 to 110° C.; 85 to 105° C.; 85 to 100° C.; 85 to 95° C.; 80 to 130° C.; 80 to 125° C.; 80 to 120° C.; 80 to 115° C.; 80 to 110° C.; 80 to 105° C.; 80 to 100° C.; 85 to 130° C.; 85 to 125° C.; 85 to 120° C.; 85 to 115° C.; 85 to 110° C.; 85 to 105° C.; 85 to 100° C.; 85 to 95° C.; 90 to 130° C.; 90 to 125° C.; 90 to 120° C.; 90 to 115° C.; 90 to 110° C.; 90 to 105° C.; 90 to 100° C.; 95 to 130° C.; 95 to 125° C.;

95 to 120° C.; 95 to 115° C.; 95 to 110° C.; 95 to 105° C.; 100 to 130° C.; 100 to 125° C.; 100 to 120° C.; 100 to 115° C.; 100 to 110° C.; 105 to 130° C.; 105 to 125° C.; 105 to 120° C.; 105 to 115° C.; 110 to 130° C.; 110 to 125° C.; 110 to 120° C.; 115 to 130° C.; 115 to 125° C.; 115 to 120° C.; 115 to 130° C.; 115 to 125° C.; 115 to 120° C.; and 120 to 130° C., as measured by ASTM Method 3418; in one embodiment, a Tg above 70° C. is preferred.

For certain embodiments of the invention, the condensation polymers, e.g.,copolyesters, useful in the invention may exhibit at least one of the following inherent viscosities as determined in 60/40 (wt/wt) phenol/tetrachloroethane at a concentration of 0.5 g/100 ml at 25° C.: one of the following ranges: 0.35 to 1.5 dL/g; 0.35 to 1.2 dL/g; 0.35 to 1 dL/g; 0.50 to 1.5 dL/g; 0.50 to 1.2 dL/g; 0.50 to 1 dL/g; 0.50 to 0.85 dL/g; 0.50 to 80 dL/g; 0.50 to 0.75 dL/g; 0.50 to less than 0.75 dL/g; 0.50 to 0.72 dL/g; 0.50 to 0.70 dL/g; 0.50 to less than 0.70 dL/g; 0.50 to 0.68 dL/g; 0.50 to less than 0.68 dL/g; 0.50 to 0.65 dL/g; 0.55 to 1.5 dL/g; 0.55 to 1.2 dL/g; 0.55 to 1 dL/g; 0.55 to 0.85 dL/g;

0.55 to 0.80 dL/g; 0.55 to 0.78 dL/g; 0.55 to 0.75 dL/g; 0.55 to less than 0.75 dL/g; 0.55 to 0.72 dL/g; 0.55 to 0.70 dL/g; 0.55 to less than 0.70 dL/g; 0.55 to 0.68 dL/g; 0.55 to less than 0.68 dL/g; 0.55 to 0.65 dL/g; 0.60 to 1.5 dL/g; 0.60 to 1.2 dL/g; 0.60 to 0.80 dL/g; 0.60 to 0.75 dL/g; 0.60 to 0.68 dL/g; 0.70 to 1.5 dL/g 0.70 to 1.2 dL/g; 0.80 to 1.5 dL/g; and 0.80 to 1.2 dL/g.

For certain embodiments of the invention, the copolyesters useful in the invention may exhibit at least one of the following inherent viscosities as determined in 60/40 (wt/wt) phenol/tetrachloroethane at a concentration of 0.5 g/100 ml at 25° C.: 0.70 to 1.2 dL/g; 0.70 to 1.1 dL/g; 0.70 to 1 dL/g; 0.70 to less than 1 dL/g; 0.70 to 0.98 dL/g; 0.70 to 0.90 dL/g; 0.70 to 0.85 dL/g; 0.70 to 0.80 dL/g; 0.70 to 1.2 dL/g; 0.70 to 1.1 dL/g; 0.70 to 1 dL/g; 0.70 to less than 1 dL/g; 0.70 to 0.98 dL/g; 0.70 to 0.90 dL/g; 0.70 to 0.85 dL/g; 0.70 to 0.80 dL/g; 0.75 to 1.2 dL/g; 0.75 to 1.1 dL/g; 0.75 to 1 dL/g; 0.75 to 0.98 dL/g; 0.75 to 0.90 dL/g; 0.75 to 0.85 dL/g; 0.80 to 1.2 dL/g; 0.80 to 1.1 dL/g; 0.80 to 1 dL/g; 0.80 to less than 1 dL/g; 0.80 to 0.98 dL/g; 0.80 to 0.90 dL/g; 0.70 to 0.80 dL/g; 0.90 to 1.2 dL/g; 0.90 to 1.1 dL/g; and 0.90 to 1 dL/g.

It is contemplated that the copolyesters of the invention can possess at least one of the inherent viscosity ranges described herein and at least one of the monomer ranges for the compositions described herein unless otherwise stated. It is also contemplated that the copolyesters of the invention can possess at least one of the Tg ranges described herein and at least one of the monomer ranges for the compositions described herein unless otherwise stated. It is also contemplated that the copolyesters of the invention can possess at least one of the Tg ranges described herein, at least one of the inherent viscosity ranges described herein and at least one of the monomer ranges for the compositions described herein unless otherwise stated.

In one embodiment, the copolyesters or polymer blends useful in the invention and/or the copolyester compositions of the invention, with or without toners, can have color values L*, a* and b* which can be determined using a Macbeth Spectrophotometer in transmission mode. The color determinations are averages of values measured on either pellets, or powders or particles less in size than 300 microns, of the polymers or plaques or other items injection molded or extruded from them. They are determined by the L*a*b* color system of the CIE (International Commission on Illumination) (translated), wherein L* represents the lightness coordinate, a* represents the red/green coordinate, and b* represents the yellow/blue coordinate, as determined by the L*a*b* color system measured following ASTM D 6290-98 and ASTM E308-99.

In certain embodiments, the initial b* color values and/or Δb* color values for the copolyesters useful in the invention, with or without the presence of dyes/colorants, can be present in one of the following ranges: −10 to 10; −10 to 9; −10 to 8; −10 to 7; −10 to 6; −10 to 5; −10 to 4; −10 to 3; −10 to 2; from −5 to 9; −5 to 8; −5 to 7; −5 to 6; −5 to 5; −5 to 4; −5 to 3; −5 to 2; 0 to 9; 0 to 8; 0 to 7; 0 to 6; 0 to 5; 0 to 4; 0 to 3; 0 to 2; 1 to 10; 1 to 9; 1 to 8; 1 to 7; 1 to 6; 1 to 5; 1 to 4; 1 to 3; and 1 to 2.

In addition, the copolyester compositions and the polymer blend compositions containing the copolyesters useful in this invention may also contain from 0.01 to 25% by weight or 0.01 to 20% by weight or 0.01 to 15% by weight or 0.01 to 10% by weight or 0.01 to 5% by weight of the total weight of the polyester composition of common additives such as colorants, toners, dyes, mold release agents, flame retardants, plasticizers, nucleating agents, stabilizers, including but not limited to, UV stabilizers, thermal stabilizers and/or reaction products thereof, fillers, and impact modifiers. Examples of typical commercially available impact modifiers include, but are not limited to, ethylene/propylene terpolymers, functionalized polyolefins such as those containing methyl acrylate and/or glycidyl methacrylate, styrene-based block copolymeric impact modifiers, and various acrylic core/shell type impact modifiers. For example, UV additives can be incorporated into articles of manufacture through addition to the bulk, through application of a hard coat, or through coextrusion of a cap layer. Residues of such additives are also contemplated as part of the polyester composition.

The copolyesters of the invention can comprise at least one chain extender. Suitable chain extenders include, but are not limited to, multifunctional (including, but not limited to, bifunctional) isocyanates, multifunctional epoxides, including for example, epoxylated novolacs, and phenoxy resins. In certain embodiments, chain extenders may be added at the end of the polymerization process or after the polymerization process. If added after the polymerization process, chain extenders can be incorporated by compounding or by addition during conversion processes such as injection molding or extrusion. The amount of chain extender used can vary depending on the specific monomer composition used and the physical properties desired but is generally about 0.1 percent by weight to about 10 percent by weight, preferably about 0.1 to about 5 percent by weight, based on the total weight of the polyester.

Thermal stabilizers are compounds that stabilize polyesters during polyester manufacture and/or post polymerization including, but not limited to, phosphorous compounds including but not limited to phosphoric acid, phosphorous acid, phosphonic acid, phosphinic acid, phosphonous acid, and various esters and salts thereof. These can be present in the copolyester compositions useful in the invention. The esters can be alkyl, branched alkyl, substituted alkyl, difunctional alkyl, alkyl ethers, aryl, and substituted aryl. In one embodiment, the number of ester groups present in the particular phosphorous compound can vary from zero up to the maximum allowable based on the number of hydroxyl groups present on the thermal stabilizer used. The term "thermal stabilizer" is intended to include the reaction products thereof. The term "reaction product" as used in connection with the thermal stabilizers of the invention refers to any product of a polycondensation or esterification reaction between the thermal stabilizer and any of the monomers used in making the polyester as well as the product of a polycondensation or esterification reaction between the catalyst and any other type of additive.

The copolyester compositions of the invention can contain reinforcing materials can include, but are not limited to, carbon filaments, silicates, mica, clay, talc, titanium dioxide, Wollastonite, glass flakes, glass beads and fibers, and polymeric fibers and combinations thereof. In one embodiment, the reinforcing materials are glass, such as, fibrous glass filaments, mixtures of glass and talc, glass and mica, and glass and polymeric fibers.

In another embodiment, the invention further relates to articles of manufacture, i.e., shaped articles, comprising any of the copolyesters, copolyester compositions and/or blends described above.

The copolyester compositions are useful in articles of manufacture, e.g., shaped articles, including, but not limited to, extruded, and/or molded articles including, but not limited to extruded, and/or molded articles including, but not limited to, injection molded articles, extruded articles, cast extrusion articles, profile extrusion articles, melt spun articles, thermoformed articles, extrusion molded articles, injection blow molded articles, injection stretch blow molded articles, extrusion blow molded articles and extrusion stretch blow molded articles. These articles can include, but are not limited to, films, bottles, containers, drinkware, medical parts, sheet and/or fibers.

Examples of potential molded articles include without limitation: medical devices such as dialysis equipment, medical packaging, healthcare supplies, commercial food-service products such as food pans, tumblers and storage boxes, baby bottles, sports bottles, water bottles, food processors, blender and mixer bowls, utensils, water bottles, crisper trays, washing machine fronts, and vacuum cleaner parts. Other potential molded articles could include, but are not limited to, ophthalmic lenses and frames. For instance, this material is envisioned to make bottles, including, but not limited to, baby bottles, sports bottles and water bottles.

In one aspect, the polyester compositions useful in the invention may be used in various types of film and/or sheet, including but not limited to extruded film(s) and/or sheet(s), compression molded film(s) and/or sheet(s), solution casted film(s) and/or sheet(s), calendered film(s) and/or sheet(s). Methods of making film and/or sheet include but are not limited to extrusion, compression molding, calendering and solution casting.

In one aspect, the invention is related to thermoformed film(s) and/or sheet(s) comprising the polyester(s) and/or polyester compositions of the invention.

In one aspect, the invention is related to articles of manufacture which incorporate the thermoformed film and/or sheet of the invention.

The films and/or sheets useful in the present invention can be of any thickness which would be apparent to one of ordinary skill in the art. In one embodiment, the film(s) of the invention have a thickness of no more than 40 mils. In one embodiment, the film(s) of the invention have a thickness of no more than 35 mils. In one embodiment, the film(s) of the invention have a thickness of no more than 30 mils. In one embodiment, the film(s) of the invention have a thickness of no more than 25 mils. In one embodiment, the film(s) of the invention have a thickness of no more than 20 mils The methods of forming the copolyesters into articles of manufacture, for example, fibers, films, molded articles, containers, and sheeting of the invention are well known in the art. The polyester compositions are useful in articles of manufacture including, but not limited to, fibers, filaments, films, sheets, containers, extruded, calendered, and/or molded articles including, but not limited to, injection molded articles, extruded articles, cast extrusion articles, profile extrusion articles, melt spun articles, thermoformed articles, extrusion molded articles, injection blow molded articles, injection stretch blow molded articles, extrusion blow molded articles and extrusion stretch blow molded articles.

The invention further relates to the film(s) and/or sheet(s) comprising the polyester compositions of the invention. The methods of forming the polyesters into film(s) and/or sheet(s) are well known in the art. Examples of film(s) and/or sheet(s) of the invention including but not limited to extruded film(s) and/or sheet(s), calendered film(s) and/or sheet(s), compression molded film(s) and/or sheet(s), solution casted film(s) and/or sheet(s). Methods of making film and/or sheet include but are not limited to extrusion, calendering, compression molding, and solution casting.

Examples of potential articles made from film and/or sheet include, but are not limited, to uniaxially stretched film, biaxially stretched film, shrink film (whether or not uniaxially or biaxially stretched), liquid crystal display film (including, but not limited to, diffuser sheets, compensation films and protective films), thermoformed sheet, graphic arts film, outdoor signs, skylights, coating(s), coated articles, painted articles, laminates, laminated articles, and/or multiwall films or sheets.

Examples of graphic arts film include, but are not limited to, nameplates, membrane switch overlays; point-of-purchase displays; flat or in-mold decorative panels on washing machines; flat touch panels on refrigerators; flat panel on ovens; decorative interior trim for automobiles; instrument clusters for automobiles; cell phone covers; heating and ventilation control displays; automotive console panels; automotive gear shift panels; control displays or warning signals for automotive instrument panels; facings, dials or displays on household appliances; facings, dials or displays on washing machines; facings, dials or displays on dishwashers; keypads for electronic devices; keypads for mobile phones, PDAs (hand-held computers) or remote controls; displays for electronic devices; displays for hand-held electronic devices such as phones and PDAs; panels and housings for mobile or standard phones; logos on electronic devices; and logos for hand-held phones.

Multiwall film or sheet refers to sheet extruded as a profile consisting of multiple layers that are connected to each other by means of vertical ribs. Examples of multiwall film or sheet include but are not limited to greenhouses and commercial canopies.

Examples of extruded articles comprising the copolyesters useful in this invention include, but are not limited to, film for graphic arts applications, outdoor signs, skylights, multiwall film, plastic film for plastic glass laminates, and liquid crystal display (LCD) films, including but not limited to, diffuser sheets, compensation films, and protective films for LCDs.

The copolyester compositions and/or polymer blend compositions of the invention can be useful in forming fibers, films, light diffusing articles, light diffusing sheets, light reflecting articles, light reflecting sheets, light emitting diodes, 3D powders or other materials, 3D articles containing powders or other materials. The extruded sheet can be further modified using typical fabrication techniques such as thermoforming, cold bending, hot bending, adhesive bonding, cutting, drilling, laser cutting, etc. to create shapes useful for application as light reflectors and/or light diffusers.

As used herein, the abbreviation "wt" means "weight". The inherent viscosity of the polymers, for example, the polyesters was determined in 60/40 (wt/wt) phenol/tetrachloroethane at a concentration of 0.5 g/100 ml at 25° C.

The following examples further illustrate how the compositions of matter of the invention can be made and evaluated and are intended to be purely exemplary of the invention and are not intended to limit the scope thereof. Unless indicated otherwise, parts are parts by weight, temperature is in degrees C. or is at room temperature, loading level is measured in units of weight percentage based on the total weight of the initial polymer composition equaling 100 weight %; and pressure is at or near atmospheric.

EXAMPLES

This invention can be further illustrated by the following examples of preferred embodiments thereof, although it will be understood that these examples are included merely for purposes of illustration and are not intended to limit the scope of the invention unless otherwise specifically indicated.

Materials and Methods

General: All experiments were carried out using dry glassware under an atmosphere of nitrogen unless otherwise noted. Reagents and solvents were purchased from commercial sources and used as received unless otherwise noted.

NMR Characterization: NMR Characterization: Proton NMR data were obtained on a Bruker Avance 500 NMR spectrometer operating at 500 MHz. The sample tube size was 5 mm, and samples were collected using either $CDCl_3$ (chloroform) or DMSO-$d^6$ (hexadeuterodimethyl sulfoxide) as the solvent. Chemical shifts are reported in parts per million ("ppm") from tetramethylsilane with the residual solvent peak as an internal reference.

Mass Spectrometry: Each of the samples were solubilized in DMSO at a concentration of 2 mg/mL. The samples were analyzed using liquid chromatography-mass spectrometry (LC-MS). The chromatographic separation was achieved using an Agilent 1290 liquid chromatograph (LC), which was fitted with an Agilent Zorbax SB-C18 (2.1×150 mm, 3.5 µm) column. The injection volume was 2 µl, and the column was maintained at 25° C. A post-column diode array detector (190 nm-600 nm) was used to detect the analytes before they eluted to the mass spectrometer.

The initial conditions of the mobile phase were 60% water with 2.5 mM NH$_4$OAc [ammonium acetate] and 40% acetonitrile (ACN). A gradient elution was performed according to the following table:

| Time | A % (H$_2$O w/ 2.5 mM NH$_4$OAc) | B % (ACN) | Flow (ml/min) |
|---|---|---|---|
| 0 | 99 | 1 | 0.3 |
| 3 | 99 | 1 | 0.3 |
| 15 | 5 | 95 | 0.3 |

Mass spectra were acquired with an Agilent QTOF 6550 mass spectrometer, which was coupled to the LC. This instrument produces data of high mass accuracy and good isotope fidelity. Using this information, the molecular formula of an unknown species can be determined. The mass spectra were collected using electrospray ionization in the negative-ion mode. Structures were proposed based on the measured accurate mass and molecular formula along with known chemistry.

EXPERIMENTAL PROCEDURES

Example 1: Process of Acylating a Diacid Chloride with an Alcohol to Form at least One Diester such as 1,4-di-tert-butyl-terephthalate, e.g. as Represented in the following Reaction

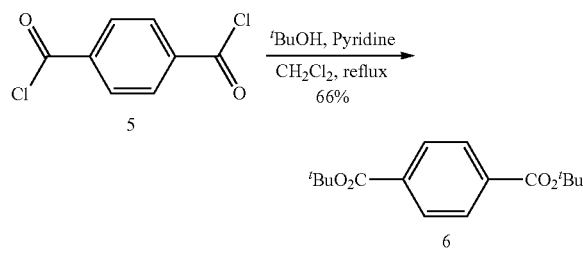

In general, the steps are as follows: In Step A of this Example 1, at least one alcohol (such as, tert-butanol), at least one base (e.g., pyridine, for example, 4-dimethylaminopyridine); and at least one aprotic solvent (e.g., methylene chloride) is added to a first reaction zone; in Step B of this Example 1, at least one aprotic solvent (e.g., methylene chloride) and at least one diacid chloride (e.g., terephthaloyl chloride) is added to a second reaction zone; and in Step C of this Example 1 the product of the first reaction zone is fed into the second reaction zone which is then stirred under reflux temperature, temperature is then adjusted to 45° C., water is added, the organic layer is removed, then washed, dried and concentrated under vacuum.

More specific steps are as follows: In a first reaction zone, a 2000-mL three-neck round bottomed flask was charged with a stir bar followed by 450 mL methylene chloride. The center neck was fitted with a reflux condenser, and the right neck was fitted with a thermocouple. Tert-butanol (191 mL) was added followed by pyridine (136 mL) with stirring at room temperature.

In a second reaction zone, a separate 32 oz. jar was charged with a stir bar followed by methylene chloride (450 mL) and terephthaloyl chloride (200 g, 985 mmol). The mixture was stirred until complete dissolution of the terephthaloyl chloride was observed. The resulting mixture was charged into a liquids addition funnel, and the funnel was mounted to the round bottom flask. The funnel was opened fully, and the terephthaloyl chloride mixture (the product of the second reaction zone) was poured into the flask (the first reaction zone) over the course of about 5 minutes. Note that this is an exothermic reaction that can cause the mixture to reflux. Once the reaction temperature in the first reaction zone begins to drop below reflux temperature, the reaction temperature was adjusted to 45° C., and the reaction was stirred for 12 hours. Once this hold time was complete, the reaction mixture was diluted with 300 mL water and allowed to cool to room temperature with stirring. The resulting mixture was transferred to a separatory funnel, and the organic layer was removed. The organic layer was then washed with 300 mL water followed by 300 mL saturated sodium bicarbonate [NaHCO$_{3(aq.)}$]. The organics were then dried with sodium sulfate and concentrated en vacuo to afford a pale yellow solid. The solid was triturated with cold hexanes and filtered. The resulting solids were dried to afford 1,4-di-tert-butyl terephthalate (diester 6) (182 g, 66% yield) as a white solid.

Using the analogous procedure, compounds S1 (di-tert-butyl cyclohexane-1,4-dicarboxylate) referred to as "S1" herein) and S2 (di-tert-butyl furan-2,5-dicarboxylate (referred to as "S2" herein) were prepared. Also, di-tert-butyl furan-2,5-dicarboxylate was prepared using an analogous procedure as well.

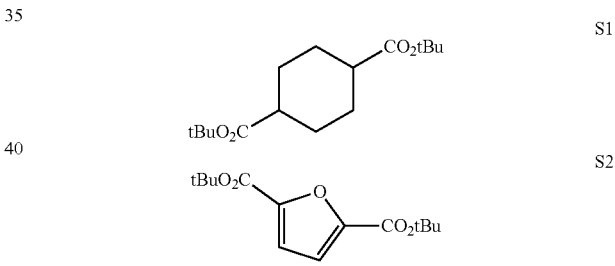

S1: Calculated for C$_{16}$H$_{28}$O$_4$: 284.20 AMU; Found: 284.20 AMU (atomic mass units) S2: Calculated for C$_{14}$H$_{20}$O$_5$: 268.13 AMU; Found:268.00 AMU Example 2: Partial Hydrolysis of the Diester Product of Example 1 to Form at least One Monoacid, e.g., 4-(tert-butoxycarbonyl)benzoic acid (7)

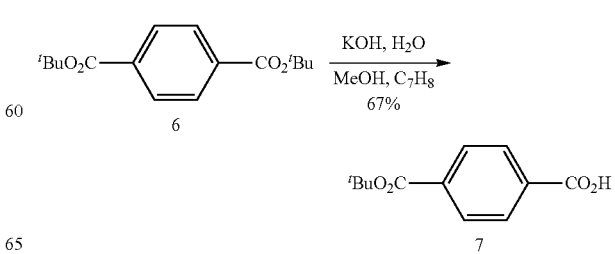

The general steps are as follows. In Step A of this Example 2, the final product of Example 1 and at least one aprotic solvent is added to a third reaction zone. In Step B of this Example 2, at least one base, water, and at least one alcohol is added to a fourth reaction zone. In Step C of this Example 2, the final contents of the fourth reaction zone are fed into the third reaction zone.

More specifically, a 2000 mL 3-neck round-bottomed flask was charged with a stir bar followed by 1,4-di-tert-butyl terephthalate (diester 6) of Example 1 (200 g, 719 mmol, 1.00 equiv). The center neck was fitted with a reflux condenser, and the right neck was fitted with a thermocouple. The flask was then charged with toluene ($C_7H_8$) (900 mL), and the mixture was allowed to stir until complete dissolution of 1,4-di-tert-butyl terephthalate was observed. In a fourth reaction zone, a separate 32 oz. jar was charged with a stir bar followed by potassium hydroxide (KOH) (40.3 g, 1.00 equiv). $H_2O$ (30.8 mL) was added to the jar, and the mixture was stirred until complete dissolution of the KOH was observed. The KOH solution was then diluted with methanol (700 mL), and the resulting mixture was added via addition funnel to the solution of 6 at room temperature. Once the addition was complete, the reaction mixture was heated to 65° C. and stirred for 3 hours. Once this hold time was complete, the reaction mixture was carefully poured into a 4 L glass beaker containing 700 mL $H_2O$. The resulting mixture was stirred for 10 minutes. The biphasic solution was transferred to a separatory funnel, and the organic layer was separated. The aqueous layer was extracted twice with (toluene) $C_7H_8$ (2×300 mL) and subsequently concentrated on a rotary evaporator to remove MeOH. The resulting solution was adjusted to pH=4.5 resulting in the formation of a white precipitate. The solids were collected by vacuum filtration, washing numerous times with water to remove residual acetic acid. The solids were then dried in a vacuum oven (60 deg. C, 22.5 mmHg) for 24 hours to afford 4-(tert-butoxycarbonyl)benzoic acid (compound 7 in the reaction shown above) as a white powder (110.6 g, 67% yield) of 4-(tert-butoxycarbonyl) benzoic acid.

$^1$H NMR (DMSO, 500 MHz) δ8.02 (dd, 4H), 1.55 (s, 9H).

Using the analogous procedure, compounds S3, and S4 were prepared.

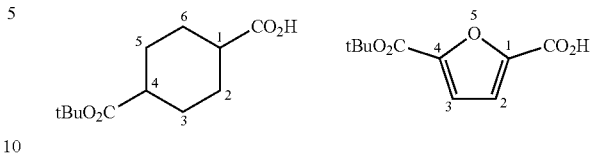

S3 (4-(tert-butoxycarbonyl)cyclohexane-1-carboxylic acid): Calculated for $C_{12}H_{20}O_4$: 228.14 AMU; Found: 228.14 AMU S4 5-(tert-butoxycarbonyl)furan-2-carboxylic acid: Calculated for $C_{10}H_{12}O_5$: 212.07 AMU; Found:212.07 AMU Examples 3 and 4

Example 3—Esterifying the Monoacid of Example 2 with at Least One Diol to Form a Diester (e.g., di-tert-butyl O,O'-(2,2,4,4-tetramethylcyclobutane-1, 3-diyl) Diterephthalate-Compound 8 in the Structure Below]

The general steps of Example 3 are as follows. The final product (the monoacid) of Example 2, at least one diol, 4-dimethylaminopyridine (DMAP), at least one aprotic solvent, and at least one carbodiimide are reacted under esterification conditions.

Example 4—Reacting the Diester (Compound 8 in the Schematic Below), the Product of Example 3, Under Reflux Conditions and with Acidic Conditions to Form a Diacid (e.g., 4,4'-(2,2,4,4-tetramethylcyclobutane-1,3-diyl)bis(oxy)bis(carbonyl)dibenzoic acid (Compound 9 in the Schematic Below)

The general steps of Example 4 are as follows. The final product (the diester) of Example 3 is reacted under reflux conditions with at least one Lewis acid, (e.g., iodine) and at least one aprotic solvent.

(1)

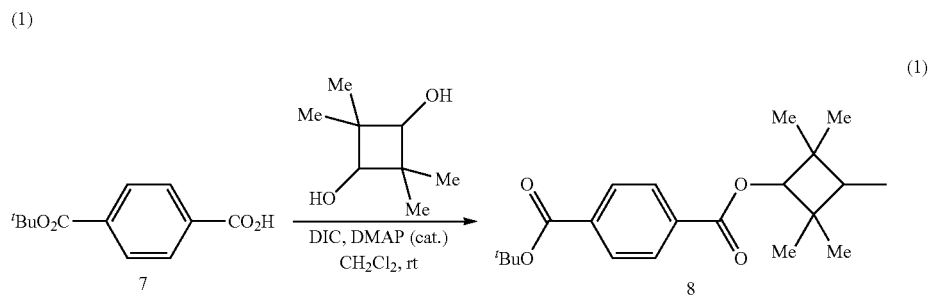

(2)

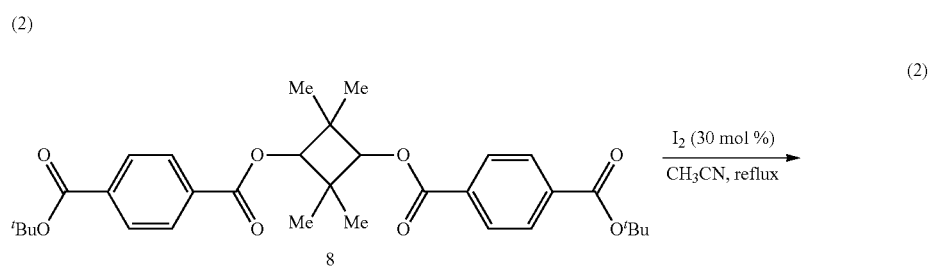

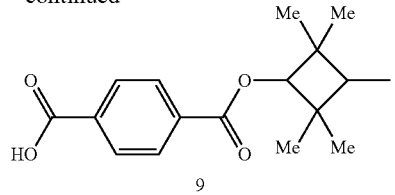

9

More specific steps for Example 3 are as follows:

Example 3—An oven-dried 2000 mL round-bottomed flask was purged under an atmosphere of $N_2$ for at least 5 minutes. The flask was then fitted with a stir bar and a rubber septum. Mono-acid 7 of Example 2, 4-(tert-butoxycarbonyl) benzoic acid, (108 g, 485 mmol, 2.00 equiv) was added to the flask followed by 2,2,4,4-tetramethyl-1,3-cyclobutane-diol (TMCD) (35 g, 243 mmol, 1.00 equiv), DMAP (4.45 g, 36.4 mmol, 0.15 equiv) and methylene chloride ($CH_2Cl_2$) (1200 mL). The stirring was started, and diisopropylcarbo-diiimide (DIC) (61.3 g, 485 mmol, 2.00 equiv) was added as a liquid over the course of 2 minutes. The resulting mixture was allowed to stir at room temperature for at least 12 hours. Once this hold time had passed, the reaction mixture was transferred to a separatory funnel. The organic layer was subsequently washed with 300 mL of brine followed by 300 mL of 10% $HCl_{(aq.)}$.

The washed organic layer was then dried with $Na_2SO_4$ and concentrated in vacuo to afford the crude ester 8 (di-tert-butyl O,O'-(2,2,4,4-tetramethylcyclobutane-1,3-diyl)diterephthalate) as a white foam which was used in the next step without further purification.

More specific steps for Example 4 are as follows:

A 2000 mL 3-neck round bottomed flask was charged with a stir bar followed by crude diester 8, (di-tert-butyl O,O'-(2,2,4,4-tetramethylcyclobutane-1,3-diyl)diterephtha-late), of Example 3 (246 mmol, 1.00 equiv), acetonitrile ($CH_3CN$) (1400 mL), and lastly 12 (18.7 g, 74 mmol, 0.30 equiv). The center neck was fitted with a reflux condenser, and the right neck was fitted with a thermocouple. The reaction mixture was subsequently heated to reflux temperature (~82° C.), and the reaction was allowed to stir until NMR analysis of a sample indicated complete consumption of the starting material (typically 12-15 hours). The resulting mixture was cooled to room temperature, upon which precipitation occurred. The solids were collected via filtration on a coarse frit whereupon they were washed successively with $CH_3CN$ until the filtrate appeared colorless. The solids were then dried in a vacuum oven (60° C., 22.5 mmHg) for at least 12 hours to afford di-acid 9, otherwise known as compound 9-[4,4'-(2,2,4,4-tetramethylcyclobutane-1,3-diyl) bis(oxy)bis(carbonyl)dibenzoic acid)] (53 g, 49% yield) as a pale pink powder.

$^1$H NMR (DMSO, 500 MHz) δ13.34 (br s, 2H), 8.10 (m, 8H), 4.71 (s, 1H), 4.59 (s, 1H), 1.37 (s, 3H), 1.24 (s, 6H), 1.15 (s, 3H).

Using the analogous procedure, compounds S5 [4,4'-di-tert-butyl O'1,O1-(2,2,4,4-tetramethylcyclobutane-1,3-diyl) bis(cyclohexane-1,4-dicarboxylate)] and S6 [5,5'-di-tert-butyl O'2,O2-(2,2,4,4-tetramethylcyclobutane-1,3-diyl)bis (furan-2,5-dicarboxylate)] were prepared using TMCD as the central diol.

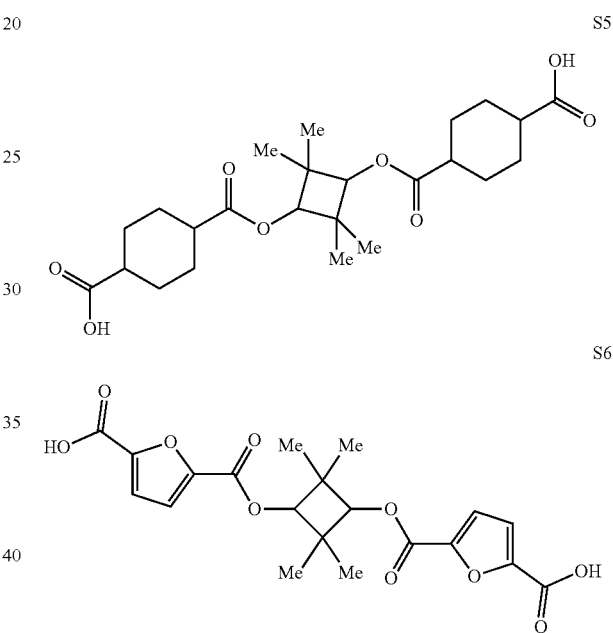

S5: Calculated for $C_{24}H_{36}O_8$: 452.24 AMU; Found: 452.24 AMU

S6: Calculated for $C_{20}H_{20}O_{10}$: 420.11 AMU; Found: 420.11 AMU

Using the analogous procedure, compounds S7 [di-tert-butyl O,O'-(cyclohexane-1,4-diylbis(methylene))ditereph-thalate], S8 [di-tert-butyl O,O'-(propane-2,2-diylbis(cyclo-hexane-4,1-diyl))diterephthalate], and S9 [O,O'-(1,3-phenylene)di-tert-butyl diterephthalate were prepared using diols CHDM (cyclohexanedimethanol), HBPA(4,4'-(pro-pane-2,2-diyl)dicyclohexanol), and resorcinol, respectively.

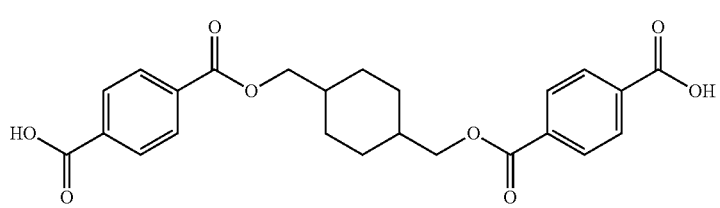

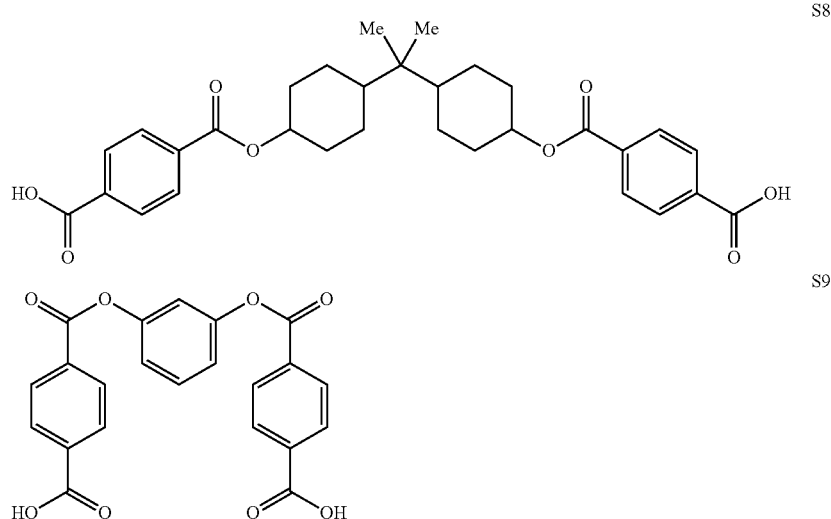

S7: Calculated for $C_{24}H_{24}O_8$: 440.15 AMU; Found: 440.15 AMU

S8: Calculated for $C_{31}H_{36}O_8$: 536.24 AMU; Found: 536.24 AMU

S9: Calculated for $C_{22}H_{14}O_8$: 406.07 AMU; Found: 406.07 AMU

The final product(s) of Example 4 can then be used in either Examples 5 or 6.

Example 5—Bisalkylation of the Diacid of Example 4 (e.g., Compound 9) with at least One Haloalcohol to Form a Pentamer The general steps of Example 5 are as follows: Dissolve the diacid of Example 4 (e.g., compound 9-[4,4'-(2,2,4,4-tetramethylcyclobutane-1,3-diyl)bis(oxy)bis(carbonyl) dibenzoic acid)] with at least one aprotic solvent, add at least one haloalcohol, and then react with at least one base to make a pentamer [e.g., bis(2-hydroxyethyl) O,O'-2,2,4,4-tetramethylcyclobutane-1,3-diyl) terephthalate].

More specific steps for Example 5 are as follows: An oven-dried 3-neck 1000 mL round-bottomed flask was purged under an atmosphere of $N_2$ for at least five minutes. The flask was then charged with di-acid 9, otherwise known as compound 9, [4,4'-(2,2,4,4-tetramethylcyclobutane-1,3-diyl)bis(oxy)bis(carbonyl)dibenzoic acid)] (48.1 g, 109 mmol, 1.00 equiv) followed by DMF (dimethylformamide) (950 mL) and a stir bar. Stirring was started, and the mixture was charged with 2-bromoethanol (40.9 g, 328 mmol, 3.00 equiv) and $K_2CO_3$ (45.3 g, 328 mmol, 3.00 equiv) in a single portion. The flask was fitted with a thermocouple, and the reaction was heated to 60 deg. C and stirred until NMR analysis confirmed complete consumption of the starting material, typically 12-15 hours. The reaction was allowed to cool to room temperature whereupon brine was added (100 mL). The mixture was transferred to a separatory funnel. Additional brine (300 mL) was added followed by $Et_2O$ (diethyl ether) (500 mL), and the mixture was extracted. The water layer was extracted three more times with 300 mL $Et_2O$, and the combined organics were returned to the

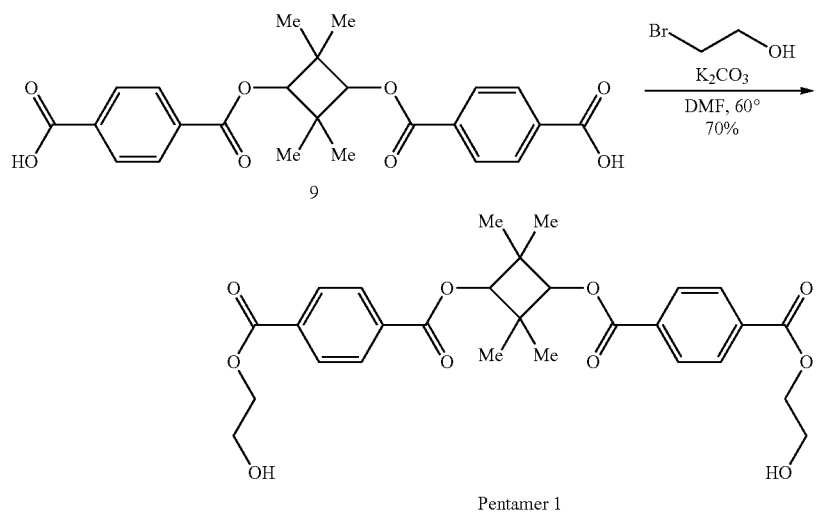

Pentamer 1 separatory funnel and washed three times with brine (3×300 mL), once with 10% HCl$_{(aq.)}$ (300 mL), and lastly twice with brine (2×300 mL). The washed organic layer was dried with Na$_2$SO$_4$ and concentrated in vacuo to afford pentamer 1 [bis(2-hydroxyethyl) O,O'-2,2,4,4-tetramethylcyclobutane-1,3-diyl) terephthalate], (42 g, 70% yield) as a pale pink-yellow solid.

$^1$H NMR (DMSO, 500 MHz) δ8.12 (m, 8H), 4.94 (br s, 2H) 4.72 (s, 1H), 4.59 (s, 1H), 4.32 (m, 4H), 3.72 (br s, 4H), 1.38 (s, 3H), 1.24 (s, 6H), 1.16 (s, 3H).

Calculated for C$_{28}$H$_{32}$O$_{10}$: 528.20 AMU; Found: 528.20 AMU

Using an analogous procedure, compounds 13 and 14 were prepared using TMCD as the central diol. Compound 13 is 4,4'-bis(2-hydroxyethyl) O'1,O1-(2,2,4,4-tetramethyl-cyclobutane-1,3-diyl)bis(cyclohexane-1,4-dicarboxylate); and Compound 14 is 5,5'-bis(2-hydroxyethyl) O'2,O2-(2,2,4,4-tetramethylcyclobutane-1,3-diyl)bis(furan-2,5-dicarboxylate).

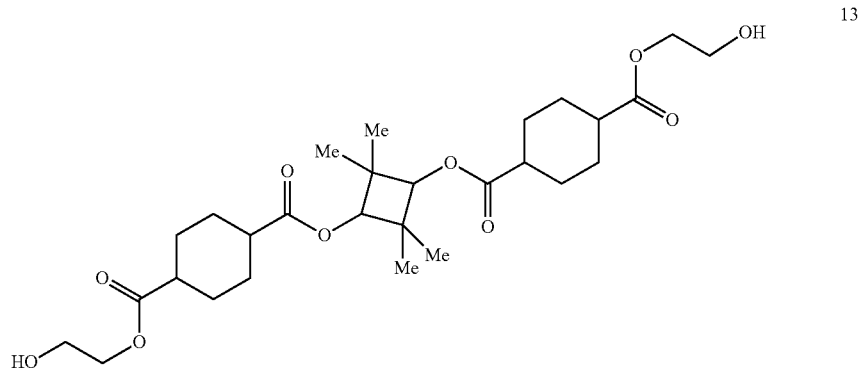

13

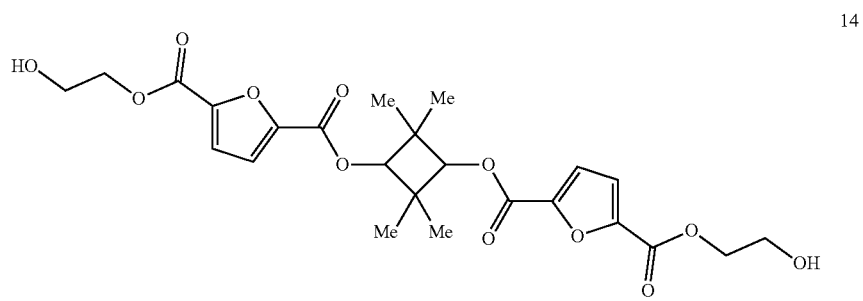

14

13: Calculated for C$_{28}$H$_{44}$O$_{10}$: 540.29 AMU; Found: 540.29 AMU

14: Calculated for C$_{24}$H$_{28}$O$_{12}$: 508.16 AMU; Found: 508.16 AMU

Using the analogous procedure, compounds 11 and 12 were prepared using CHDM and HBPA as the central diols, respectively. Compound 11 is bis(2-hydroxyethyl) O,O'-(propane-2,2-diyl bis(cyclohexane-4,1-diyl))diterephthalate and Compound 12 is O,O'-(cyclohexane-1,4-diylbis(methylene))bis(2-hydroxyethyl)diterephthalate

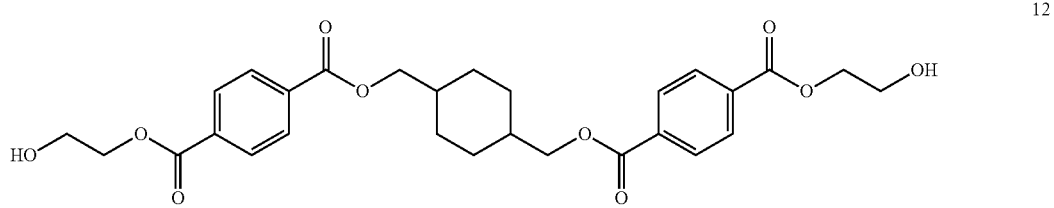

12

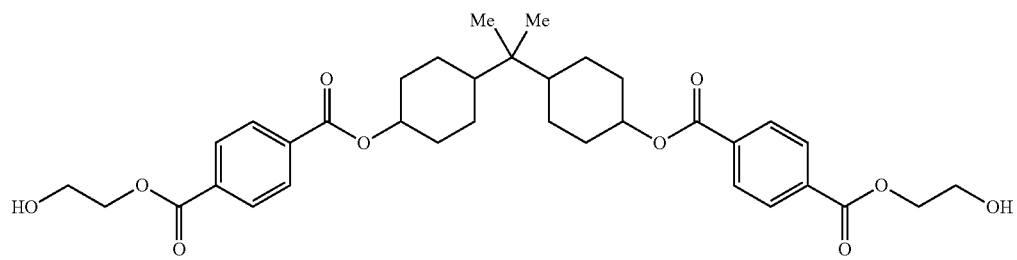

12: Calculated for $C_{28}H_{30}O_{10}$: 528.20 AMU; Found: 528.20 AMU

11: Calculated for $C_{35}H_{44}O_{10}$: 624.29 AMU; Found: 624.29 AMU

Example 6— Esterifying the Diacid of Example 4 (compound 9) Under Esterification Conditions with at least One Diol to Form a Pentamer Compound 10 [O,O'-(1,3-phenylene)bis(2-hydroxyethyl) diterephthalate] below was prepared via the following procedure. An oven-dried 20-mL scintillation vial was charged with a stir bar and diacid S9, otherwise known as compound 9-[4,4'-(2,2,4,4-tetramethylcyclobutane-1,3-diyl)bis(oxy) bis(carbonyl)dibenzoic acid)] (0.5 g, 1.23 mmol), and the vial was purged under an atmosphere of nitrogen. The vial was then charged with DMF (5 mL) followed by DMAP (0.023 g), ethylene glycol (0.191 g, 2.5 equiv), and lastly DIC (0.479 mL, 2.5 equiv). The reaction mixture was allowed to stir at room temperature for 12 hours. Following this time period, the mixture was transferred to a separatory funnel and diluted with $Et_2O$ (40 mL) and brine (40 mL). The aqueous layer was extracted with $Et_2O$ (3×20 mL), and the combined organic extracts were washed with brine (2×20 mL) followed by 1 $M_{(aq.)}$ hydrochloric acid (15 mL), dried with sodium sulfate and concentrated in vacuo to afford the title compound 10 [O,O'-(1,3-phenylene)bis(2-hydroxyethyl)diterephthalate] as a white foam.

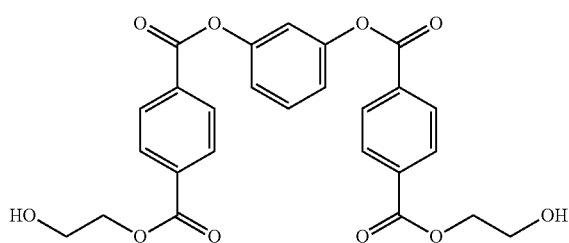

10: Calculated for $C_{26}H_{22}O_{10}$: 494.12 AMU; Found: 494.12 AMU

The invention has been described in detail with reference to the embodiments described herein, but it will be understood that variations and modifications can be effected within the scope of the invention.

What is claimed:

1. A process for making a polycondensation pre-polyester, a polyester, or both, comprising the following steps:
   A. Acylation of at least one diacid chloride to form at least one diester, comprising the following steps:
      1. Adding at least one alcohol, at least one base, and optionally, at least one aprotic solvent to a first reaction zone;
      2. Adding at least one aprotic solvent and at least one diacid chloride to a second reaction zone;
      3. Feeding the contents in the first reaction zone into the second reaction zone;
   B. Partial hydrolysis of the diester product of Step A to form at least one monoacid comprising the following steps:
      1. Adding the product of Step A and at least one aprotic solvent to a third reaction zone;
      2. Adding at least one base, water, and at least one alcohol to a fourth reaction zone;
   3. Feeding the contents in the fourth reaction zone into the third reaction zone; and
   C. Esterifying the monoacid of Step B to form a diester comprising the following steps:
      1. Adding the monoacid of Step B, at least one diol, at least one catalyst, at least one aprotic solvent and at least one carbodiimide and reacting under esterification conditions;
   D. Reacting the diester of Step C and with acidic conditions to form a diacid, comprising the following steps:
      1. Reacting the diester of Step C with at least one acid, and at least one aprotic solvent; and then performing either Step E or Step F as follows:
   E. Bisalkylation of the diacid of Step D to form a pentamer comprising the following step: dissolve the diacid of Step D in at least one aprotic solvent, add at least one base, and then react with at least one haloalcohol; or
   F. Esterifiying the diacid of Step D to form a pentamer comprising the following step: dissolve the diacid of Step D in at least one aprotic solvent and react with at least one diol and at least one carbodiimide with at least one catalyst, provided that the diol is not the same as in Step C.

2. The process of claim 1 wherein at least one diacid chloride of Step A is selected from the group consisting of terephthaloyl chloride, isophthaloyl chloride, cyclohexane-1,4-dicarbonyl chloride, furan-2,5-dicarbonyl chloride, adipoyl chloride, and sebacoyl chloride.

3. The process of claim 1 wherein the alcohol of Step A(1) is selected from the group consisting of tert-butanol, methanol, ethanol and benzyl alcohol; wherein the base of Step A(1) is at least one base is selected from 4-dimethylaminopyridine, triethylamine or diisopropylethylamine; wherein the aprotic solvent of Steps A(1) and (2) is selected from the group consisting of methylene chloride, hexane, benzene, toluene, 1,4-dioxane, chloroform, diethyl ether, dichloromethane, N-methylpyrrolidone, tetrahydrofuran, ethyl acetate, acetone, dimethylformamide, acetonitrile, and dimethyl sulfoxide; or wherein the aprotic solvent of Steps A(1) and (2) is methylene chloride.

4. The process of claim 1 wherein the catalyst of Steps C or F is 4-dimethylaminopyridine.

5. The process of any one of claims 1-3 wherein the diester product of step C is 1,4-di-tert-butyl terephthalate diester.

6. The process of claim 1 wherein the aprotic solvent of Step B(1) and (2) is selected from the group consisting of methylene chloride, toluene, tetrahydrofuran, acetonitrile, dioxane and acetone.

7. The process of claim 1 wherein the base of Step B(2) is selected from potassium hydroxide or sodium hydroxide.

8. The process of claim 1 wherein the alcohol of Step B is selected from the group consisting of tert-butanol, methanol, ethanol and benzyl alcohol.

9. The process of claim 1 wherein at least one monoacid of Steps B or C is selected from 4-tert-butoxycarbonyl) benzoic acid, 4-(tert-butoxycarbonyl)cyclohexane-1-carboxylic acid), or 5-(tert-butoxycarbonyl)furan-2-carboxylic acid, tert-methoxycarbonyl)benzoic acid, 4-(tert-methoxycarbonyl)cyclohexane-1-carboxylic acid), 5-(tert-methoxycarbonyl)furan-2-carboxylic acid, tert-ethoxycarbonyl)benzoic acid, 4-(tert-ethoxycarbonyl)cyclohexane-1-carboxylic acid), 5-(tert-ethoxycarbonyl)furan-2-carboxylic acid, tert-benzyloxycarbonyl)benzoic acid, 4-(tert-benzyloxycarbonyl)cyclohexane-1-carboxylic acid), 5-(tert-benzyloxycarbonyl)furan-2-carboxylic acid.

10. The process of claim 1 wherein the dial of Step C is selected from residues of 2,2,4,4-tetramehylcyclobutane-1,3-diol, 2,2-dimethyl-1,3-propanediol, 1,2-cyclohexanedimethanol, 1,3-cyclohexanedimethanol, 1,4-cyclohexanedimethanol, 2,2,4-trimethyl-1,3-pentanediol, hydroxypivalyl hydroxypivalate, 2-methyl-1,3-propanediol, 2-butyl-2-ethyl-1,3-propanediol, 1,4-butanediol, 1,3-propanediol, 1,5-pentanediol, 1,6-hexanediol, ethylene glycol, diethylene glycol, triethylene glycol, isosorbide, 3-methyl-pentanediol, 2-methylpentanediol, 2,2,4-tri-methylpentane-diol, 2-ethylhexanediol, 2,2-diethylpropanediol, 1,4-di-(hydroxyethoxy)-benzene, 2,2-bis-(4-hydroxycyclohexyl)-propane, 2,4-dihydroxy-1,1,3,3-etramethylcyclobutane, 2,2-bis-(3-hydroxyethoxyphenyl)-propane, resorcinol, 4,4'-(propane-2,2-diyl)dicyclohexanol or 2,2-bis-(4-hydroxypropoxyphenyl)-propane.

11. The process of claim 1, wherein at least one carbodiimide of Step C is selected from diisopropylcarbodiimide and dicyclohexylcarbodiimide.

12. The process of claim 1, wherein the aprotic solvent of Step C is selected from methylene chloride or dimethylformamide.

13. The process of claim 1, wherein at least one aprotic solvent of Step D is selected from hexane, benzene, toluene, 1,4-dioxane, chloroform, diethyl ether, dichloromethane, N-methylpyrrolidone, tetrahydrofuran, ethyl acetate, acetone, dimethylformamide, acetonitrile or dimethyl sulfoxide.

14. The process of claim 1 comprising the following step E: dissolving the diacid of Step D with at least one aprotic solvent, 4-dimethylaminopyridine, and reacting with at least one haloalcohol and at least one carbodiimide selected from diisopropylcarbodiimide and dicyclohexylcarbodiimide.

15. The process of claim 1, wherein the aprotic solvent of Step E is dimethylformamide.

16. The process of claim 1, wherein at least one base of Step E is selected from potassium carbonate, sodium carbonate, or cesium carbonate.

17. The process of claim 1, wherein at least one haloalcohol of Step E is selected from a bromoalcohol or a chloroalcohol.

18. The process of claim 17, wherein at least one haloalcohol of Step E is selected from 2-bromoethanol, 3-bromopropanol, 4-bromobutanol, 5-bromopentanol, 6-bromohexanol, 2-chloroethanol, 3-chloropropanol, 4-chlorobutanol, 5-chloropentanol, or 6-chlorohexanol.

19. The process of claim 1, wherein the diol of Step F is selected from at least one of 2,2,4,4-tetramethylcyclobutane-1,3-diol, 2,2-dimethyl-1,3-propanediol, 1,4-cyclohexanedimethanol, ethylene glycol, propylene glycol, 1,3-propanediol, and butanediol.

20. The process of claim 1, wherein the pentamer of Step E or F is O,O'-(1,3-phenylene)bis(2-hydroxyethyl)diterephthalate).

\* \* \* \* \*

UNITED STATES PATENT AND TRADEMARK OFFICE
CERTIFICATE OF CORRECTION

| | | |
|---|---|---|
| PATENT NO. | : 12,215,186 B2 | Page 1 of 1 |
| APPLICATION NO. | : 17/596690 | |
| DATED | : February 4, 2025 | |
| INVENTOR(S) | : Robert Jacks Sharpe and Emmett Dudley Crawford | |

It is certified that error appears in the above-identified patent and that said Letters Patent is hereby corrected as shown below:

In the Claims

Column 41, Line 41, Claim 10 "1,1,3,3-etramethylcyclobutane" should read --1,1,3,3-tetramethyl-cyclobutane--.

Signed and Sealed this
Twenty-second Day of July, 2025

Coke Morgan Stewart
*Acting Director of the United States Patent and Trademark Office*